United States Patent
Swett

(10) Patent No.: US 11,635,369 B1
(45) Date of Patent: Apr. 25, 2023

(54) MINIATURE FT-MIR USING A MEMS INTERFEROMETER WITH A METASURFACE EMITTER AND DETECTOR

(71) Applicant: Saudi Arabian Oil Company, Dhahran (SA)

(72) Inventor: Dwight W. Swett, Cypress, TX (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/453,290

(22) Filed: Nov. 2, 2021

(51) Int. Cl.
*G01N 21/00* (2006.01)
*G01N 21/35* (2014.01)

(52) U.S. Cl.
CPC ..... *G01N 21/35* (2013.01); *G01N 2021/3595* (2013.01); *G01N 2201/0221* (2013.01)

(58) Field of Classification Search
CPC ........ G01N 21/35; G01N 21/00; G01N 29/46; G01N 2021/3595; G01N 2201/0221; G01J 3/45
See application file for complete search history.

(56) References Cited

U.S. PATENT DOCUMENTS

| 7,796,267 B2 | 9/2010 | Saadany et al. |
| 8,531,675 B2 | 9/2013 | Khalil et al. |
| 2011/0139990 A1 | 6/2011 | Xie et al. |
| 2016/0231172 A1* | 8/2016 | Medhat .............. G02B 26/0841 |
| 2020/0182781 A1* | 6/2020 | Sadek .................. G01N 21/359 |

OTHER PUBLICATIONS

U.S. Appl. No. 17/453,285, Swett, filed Nov. 2, 2021.
U.S. Appl. No. 62/946,363, Swett, filed Dec. 10, 2020.
Aske et al., "Determination of saturate, aromatic, resin, and asphaltenic (sara) components in crude oils by means of infrared and near-infrared spectroscopy," Energy & Fuels, Aug. 2001, (15)1304-1312, 9 pages.
Chai, "Review of MEMS Based Fourier Transform Spectrometers," Micromachines, 11, 214, Feb. 2020, 28 pages.
comsol.com [online], "MultiPhysics simulation software," available on or before Dec. 31, 2021, via Internet Archive: Wayback Machine URL <http://web.archive.org/web/20211231000821/https://www.comsol.com/comsol-multiphysics>, retrieved on Feb. 14, 2022, <https://www.comsol.com/comsol-multiphysics>, 9 pages.
Feng and Halterman, "Perfect absorption in ultrathin epsilon-near-zero metamaterials induced by fast-wave non-radiative modes," American Physical Society, Phys. Rev. B, Oct. 2012, 86: 165103-1, 6 pages.
Jin et al., "Arbitrarily thin metamaterial structure for perfect absorption and giant magnification," Optics Express, 2011, 19(12): 11114-11119, 6 pages.

(Continued)

*Primary Examiner* — Abdullahi Nur
(74) *Attorney, Agent, or Firm* — Fish & Richardson P.C.

(57) ABSTRACT

A miniature Fourier transform mid-infrared (FT-MIR) spectrometer is provided. The FT-MIR includes a metasurface IR source to emit radiation when heated, a microelectromechanical (MEMS) interferometer, and a metasurface microbolometer to measure an interferogram from the MEMS interferometer, wherein the miniature FT-MIR spectrometer is less than about 20 mm in outer diameter.

30 Claims, 29 Drawing Sheets

(56) References Cited

OTHER PUBLICATIONS

Li et al., "Miniature Fourier transform spectrometer based on wavelength dependence of half-wave voltage of a LiNbO3 waveguide interferometer," Opt. Lett., Jun. 2014, 39(13):3923-3926, 4 pages.
Parashar et al., "Three Cavity Tunable MEMS Fabry Perot Interferometer," Sensors, 7, 3071-3083, Dec. 2007, 14 pages.
Pergament et al., "Vanadium dioxide: Metal-insulator transition, electrical switching and oscillations, a review of state of the art and recent progress," Energy Materials and Nanotechnology (EMN) Meeting on Computation and Theory, Nov. 2015, 25 pages.
Souza et al., "Fourier transform spectrometer on silicon with thermo-optic non-linearity and dispersion correction," Nat. Commun., Feb. 2018, 9:665, 8 pages.
Swett, "Near Centimeter-scale FT-MIR Spectrometer based on NZIM Perfect Absorption using Inverted TanCirc Conformal Mapping Geometry," Research Square, Nov. 16, 2021, 19 pages.
Swett, "Near zero index perfect metasurface absorber using inverted conformal mapping," Scientific Reports 10, 2020, 9731, 14 pages.
Takami et al., "High temperature-coefficient of resistance at room temperature in w-doped vo2 thin films on al2o3 substrate and their thickness dependence," Japanese Journal of Applied Physics, May 2011, 50(5R):055804, 4 pages.
Zheng et al., "High-resolution on-chip spectrometer with a tunable micro-ring resonator filter," Conf. Lasers ElectroOpt. 2, Jun. 2016, 2016 AM1J.2, 2 pages.
Zhong et al., "Perfect absorption in ultrathin anisotropic E-near-zero metamaterials," Applied Physics Letters, 2014, 105(1): 023504, 5 pages.

\* cited by examiner

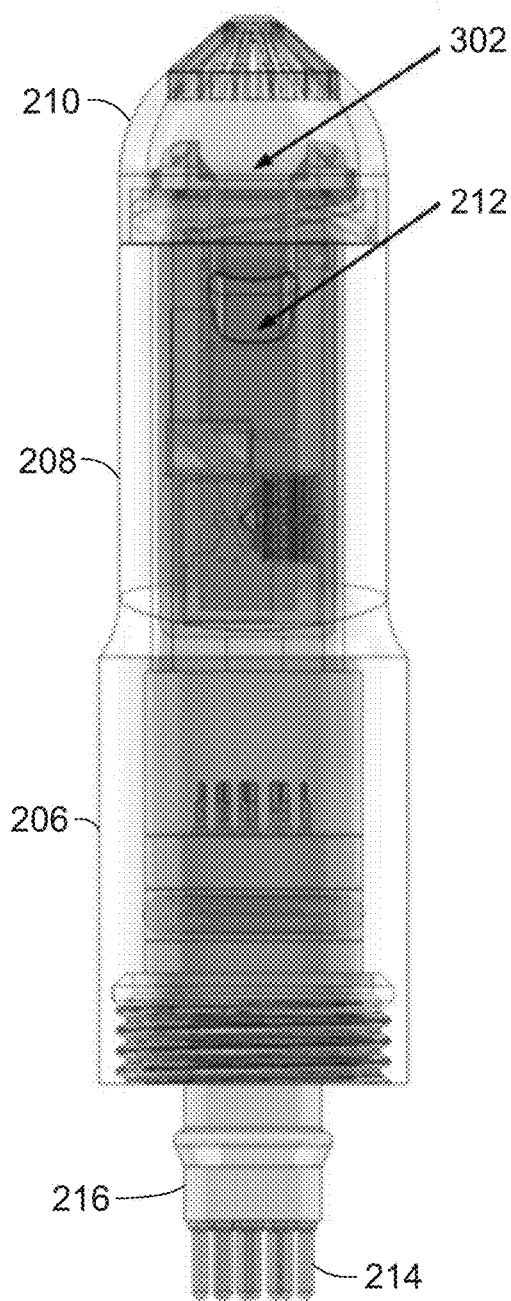
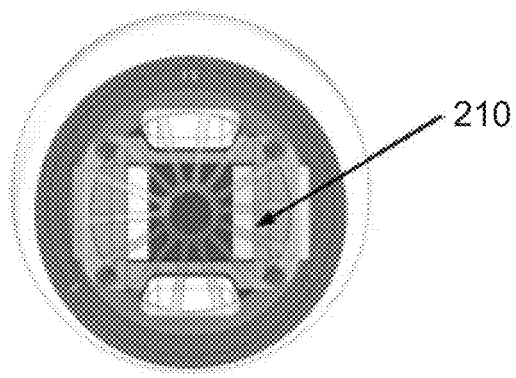
FIGURE 3A
FIGURE 3B

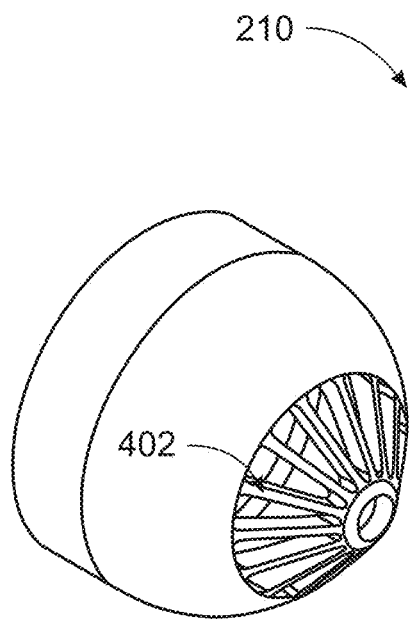
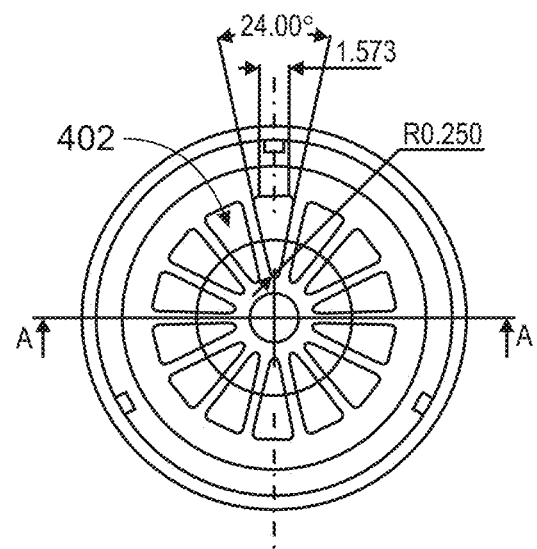
FIGURE 4A  FIGURE 4B
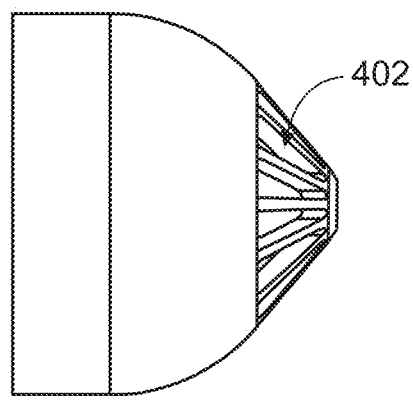
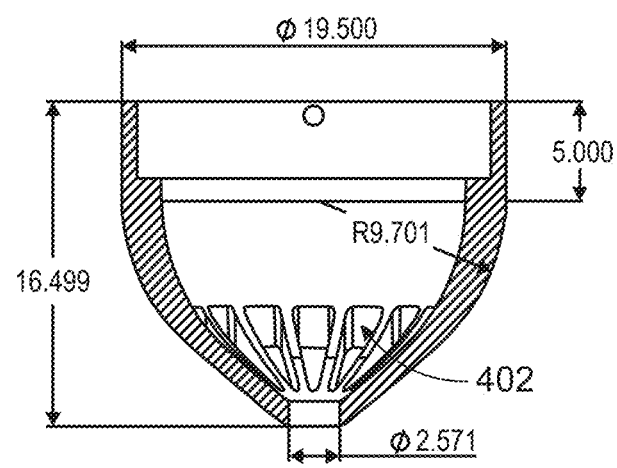
FIGURE 4C  FIGURE 4D

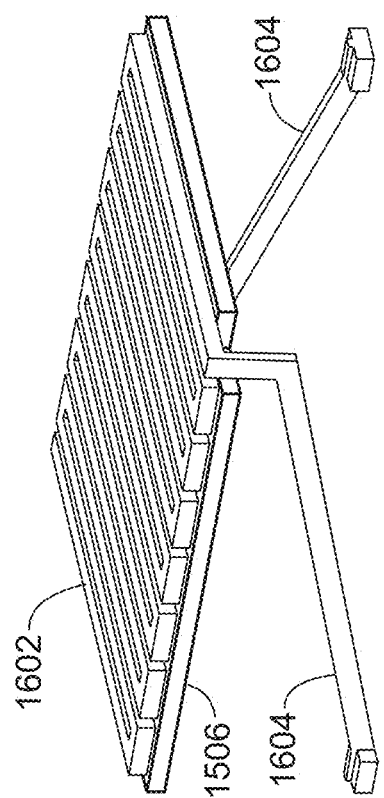
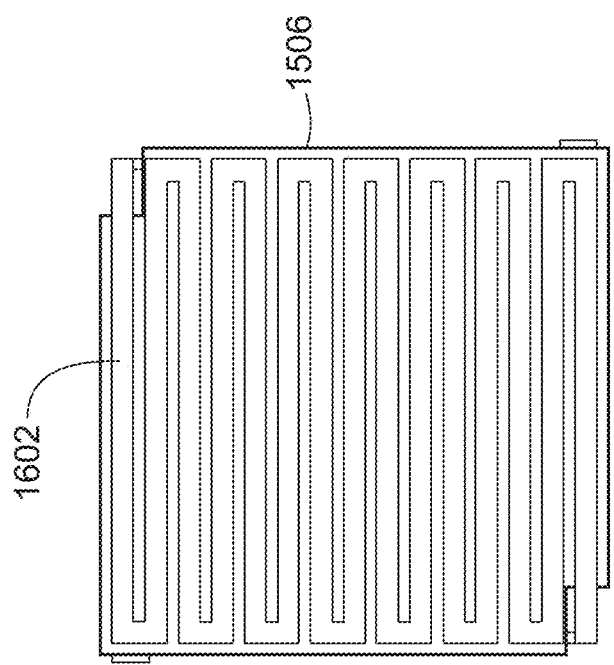
FIGURE 16B
FIGURE 16A

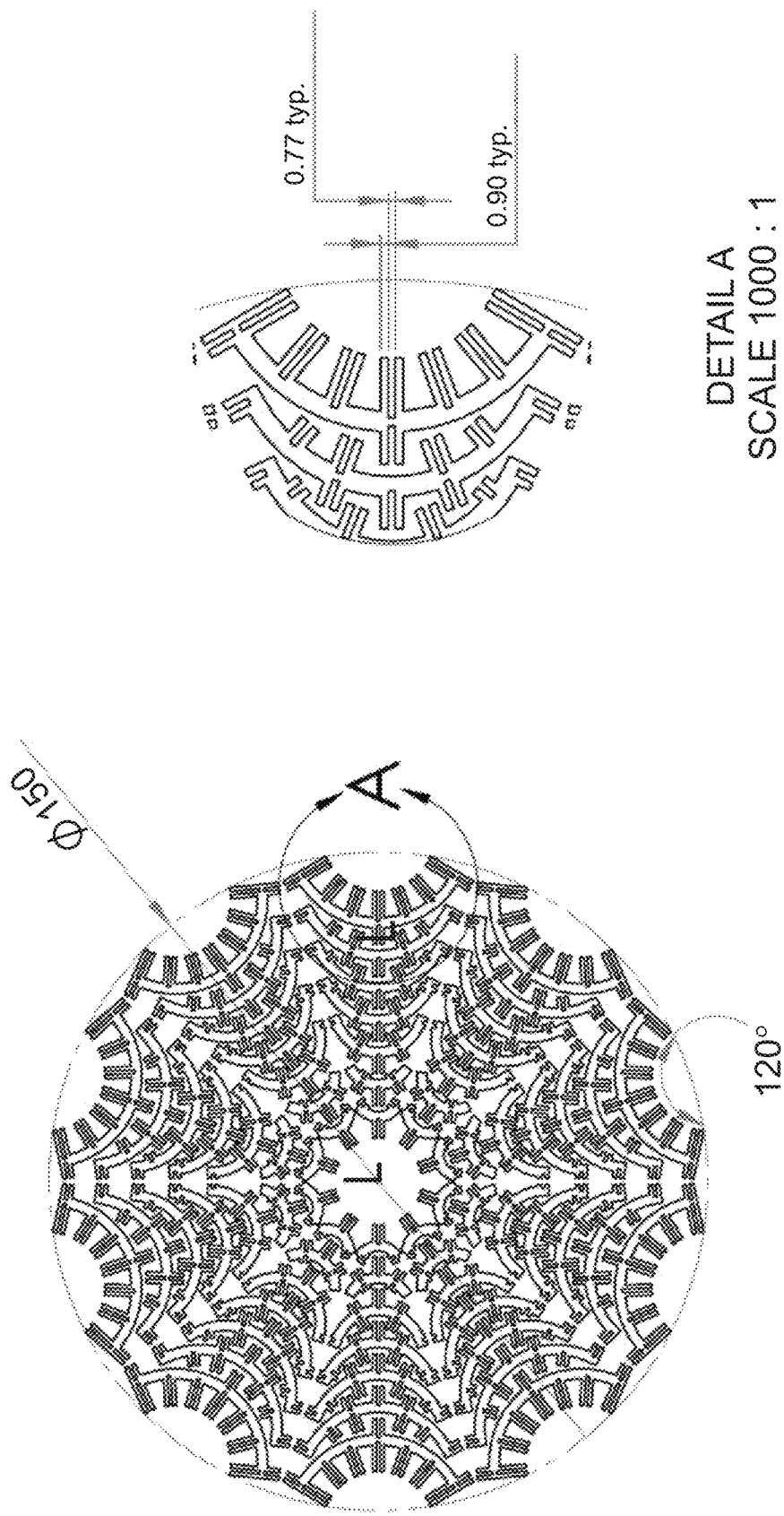

MINIATURE FT-MIR USING A MEMS INTERFEROMETER WITH A METASURFACE EMITTER AND DETECTOR

TECHNICAL FIELD

The present disclosure is directed to a miniature Fourier transform infrared spectrometer active in the mid-IR region or FT-MIR. More specifically, the FT-MIR uses an interferometer based on a micro-electromechanical system (MEMS) used in conjunction with an uncooled near-zero index metasurface source and detector.

BACKGROUND

Infrared spectrometers have been deployed in a wide range of applications that benefit from non-invasive chemical analysis. For the oil & gas industry, the potential to migrate this technology into downhole logging application holds important benefits in the identification and analysis of in situ hydrocarbons particularly with respect to the mid-infrared regime, which could allow real-time chemical analysis and quantification of saturate, aromatic, resin, and asphaltenic (SARA) components. However, the constraints on size and thermal control with existing miniaturization applications are relatively benign in comparison to those for downhole, which have been a significant obstacle to migration of the technology into oilfield sensing applications. For instance, the environmental conditions in downhole logging while drilling operations can exceed 175° C. and 200 MPa with sensor packages confined to less than a few centimeters in diameter. While production logging conditions are more benign, generally less than 125° C. and 100 MPa, still sensor packages less than a couple of centimeters in diameter are required. None of these type of downhole applications are amenable to integration of the cryogenic cooling systems typical with laboratory grade detectors.

SUMMARY

An embodiment described in examples herein provides a miniature Fourier transform mid-infrared (FT-MIR) spectrometer. The FT-MIR includes a metasurface IR source to emit radiation when heated, a microelectromechanical (MEMS) interferometer, and a metasurface microbolometer to measure an interferogram from the MEMS interferometer, wherein the miniature FT-MIR spectrometer is less than about 20 mm in outer diameter.

BRIEF DESCRIPTION OF DRAWINGS

FIGS. 3A and 3B are side and top views of the FT-MIR showing the path of wellbore fluids through the flow-through shroud.

FIGS. 4A to 4D are different views of the flow-through shroud, showing dimensions that may be used in various embodiments.

FIGS. 16A and 16B are drawings of the heating filament for the metasurface source array of FIG. 15.

FIGS. 19A to 19D are drawings showing a metasurface geometry of the microbolometer or detector based on Rhodonea conformal mapping contours.

DETAILED DESCRIPTION

Figure 1:
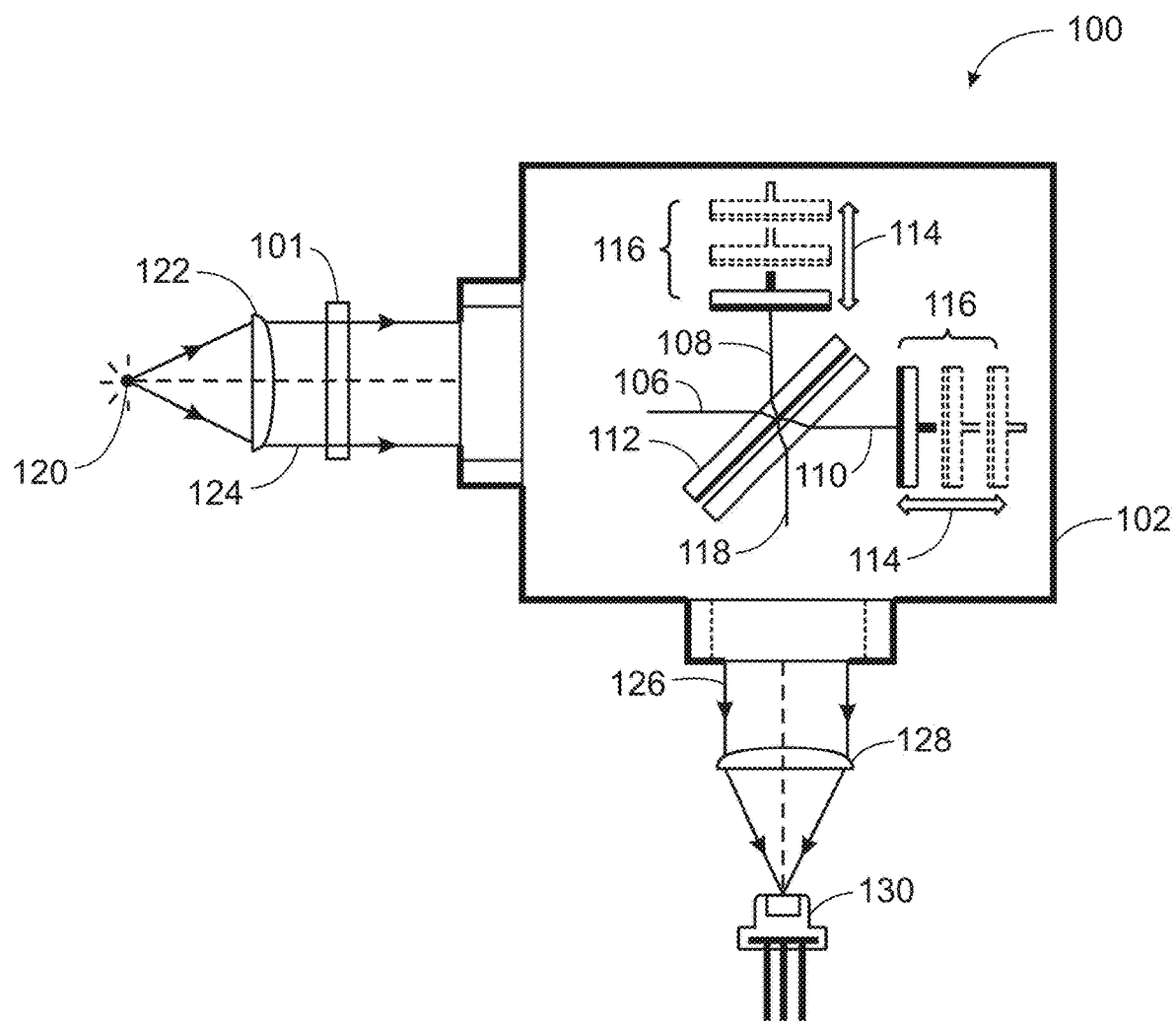
FIG. 1 is a schematic diagram of a representative Fourier transform infrared (FTIR) spectrometer.

Conventional lab grade FT-IR spectrometers are bulky devices comparable in size to a desktop computer and can cost more than $100,000 to purchase. A long sought after objective of MEMS research is the realization of an "FT-IR on a chip" which could enable laboratory grade chemical spectroscopy instrumentation to be accessible on a millimeter-scale device at a fraction of the cost of a conventional lab benchtop instrument. Such a miniaturized infrared spectrometer would have applications in medical analysis and treatment, security screening, food quality control, and remote sensing including in situ downhole chemical analysis.

Studies have suggested that successful development of a mid-IR (MIR) spectroscopic device for down-hole application in the petroleum industry holds many potentially attractive benefits with respect to the identification and analysis of downhole hydrocarbons, particularly with respect to quantification of saturate, aromatic, resin, and asphaltenic (SARA) components, as well as emulsion analysis. However, existing MIR spectrometers rely on cryogenic cooling for the detectors and remain confined to laboratory applications. Further, the large sizes of current MIR units would prevent them from downhole application.

The majority of on-chip spectrometers proposed to date have been dispersive designs, which use gratings or microresonators to separate certain wavelengths of broadband light in a spectral range and direct each wavelength individually to a detector. These designs suffer from inherent signal-to-noise ratio (SNR) penalties due to spreading the input light beam over many spectral channels making these unsuitable for high-resolution downhole chemical analysis applications. Non-dispersive instruments, such as FT-IR spectrometers, do not separate out the individual wavelengths of the broadband light source and retain what is called the multiplex advantage with a significantly higher SNR compared to dispersive designs. Benchtop FT-IR spectrometers utilize this nondispersive approach in an optical design incorporating moveable mirrors to generate an optical path length (OPL) difference, providing an interferogram that can be processed by Fourier transform (FT) processing into a wavelength spectrum. However, proposed on-chip FT-IR spectrometer designs have been unable to translate the high-resolution laboratory optical design into a miniaturized package. Instead, on-chip FT-IR interferometers that have been proposed rely on thermo-optic or electro-optic modulation to change the OPL in a waveguide. The very small refractive index modifications produced by these modulation effects, however, result in large device footprints and constrain the practically attainable spectral resolution to tens of wave numbers, which is not sufficient for downhole chemical spectroscopic applications. Chemical analysis in downhole applications will need wavenumber resolution on the order of 10 $cm^{-1}$, e.g., 10 $cm^{-1}$ to 20 $cm^{-1}$ to discriminate between various elements and compounds of interest.

Further, current on-chip concepts that have been proposed are strictly interferometer designs, which require the additional integration of an interface with an external broadband light source as well as sample interface optics. Technically these devices do not constitute stand-alone spectrometers. Thus, the current concepts do not integrate the infrared source and sample interface optics on-chip, and, as a result, remain too large for downhole applications.

Embodiments described herein provide an FT-IR with a centimeter-scale and a mid-IR range, termed a miniature FT-MIR spectrometer herein, for deployment into downhole chemical analysis applications. As described herein, the instrument includes a number of developments to decrease the size. The miniature FT-MIR uses a novel metasurface geometry to develop an infrared source on a chip in combination with a MEMS interferometer that has an embedded metasurface detector that does not require cooling for use in the mid-IR, for example, about 500 $cm^{-1}$ to about 2000 $cm^{-1}$.

The metasurface infrared source and uncooled metasurface microbolometer detector are made possible by perfect metasurface absorber (PMA) properties formed from a set of inverted conformal mapping contours of the Rhodonea, or more commonly four-leaf roses, conformal mapping. The PMA behaves as a near zero index metamaterial (NZIM) having intrinsic multiple coupled absorption resonances that combine to form broadband infrared absorption characteristics of more than 90% in the wavenumber range 1500-600 $cm^{-1}$. An uncooled microbolometer design is described that uses the metasurface geometry imprinted on a $Si_3N_4$ dielectric substrate with a $VO_2$ thermometric substrate providing a mid-IR detector with predicted maximum absorption of 99.5% at 870 $cm^{-1}$ and an absorption bandwidth of 156% full-width half-maximum (FWHM) on 1070 $cm^{-1}$ center wavenumber. These wavenumbers are coincident with important chemical spectra of downhole hydrocarbon fluids and emulsions.

Figures of merit analyses for the uncooled microbolometer result in predicted maximum detectivity $D^* = 1.0 \times 10^{10}$ cm $\sqrt{Hz}/W$ and noise equivalent difference temperature NEDT of 1 mK at a modulation frequency of 500 Hz and a microbolometer temperature of 60° C. The uncooled microbolometer parameters support the miniaturization of the mid-IR interferometers and enables the use of in situ FT-MIR spectroscopy in downhole application. The disclosed miniature spectrometer invention fits within a 1500 $mm^3$ envelope (<Ø16 mm) compatible with a range of downhole application modes including a multi-sensor array production logging tool. The miniature FT-MIR spectrometer is projected to deliver a spectral resolution of 12.7 $cm^{-1}$ at a 1.5 Hz sampling rate over the mid-IR bandwidth 600-2000 $cm^{-1}$. This is compatible with the performance found in standard laboratory grade spectroscopic instruments having spectral resolutions between 4-16 $cm^{-1}$ in the mid-IR bandwidth, using a two-minute sampling time, but occupying volumetric envelopes more than $10^5$ times larger (622×653×533 $mm^3$).

FIG. 1 is a schematic diagram of a representative Fourier transform infrared (FTIR) spectrometer 100. Fourier transform infrared spectroscopy generally uses an interferometer, for example, a Michelson interferometer to collect data on a sample 101 based on path length differences. In various embodiments described herein, the Michelson interferometer is based on a microelectromechanical system (MEMS), which is termed a MEMS interferometer 102. After collection, the data is processed using a Fourier transform resulting in an IR spectrum. Although the sample 101 is shown as being measured by light transmission, in various embodiments described herein, the sample 101 is measured by attenuated total reflection.

The operation of the MEMS interferometer 102 is based upon separating an incident or input beam 106 of radiation into two beams 108 and 110 by means of a beamsplitter 112. A path length difference between the separated beams is introduced by antisymmetric movement 114 of both of two reflecting elements, for example, a pair of mirrors 116. The path length difference creates constructive and destructive interference in the recombined beam 118 at the beamsplitter 112.

Thus, radiation originating from a source 120 passes through input optics 122, forming an approximately collimated input beam 124. The approximately collimated input beam 124 passes through the sample 101 and into the MEMS interferometer 102. The constructive and destructive interference of the recombined beam 118 results in a change in the intensity of the output beam 126 as a function of the relative path length difference, termed an interferogram. The output beam 126 is passed through output optics 128 to be focused on a detector 130 to measure the interferogram, such as the metasurface microbolometer described herein.

The intensity of the interferogram can be monitored as a function of path difference, for example, the relative displacement of the reflecting elements over time, using the detector 130. Fourier transformation techniques are applied to the raw interferogram data to convert the spectra from the relative displacement domain to the wavelength domain, resulting in an absorption spectrum. The absorption spectra can be analyzed to determine the chemical composition of the sample.

Decreasing the size of these instruments is a prerequisite to their widespread deployment in remote sensing applications such as downhole production logging systems. Consequently, miniaturization schemes for infrared spectrometers have been the focus of much research over the last several years, particularly with regard to micro-electronics chip-scale approaches, but remains confronted by three main challenges, the development of laboratory grade spectroscopy without the need for cryogenically cooled detector technologies, the miniaturization of the infrared source and interferometer assembly down to a scale amenable with integration into downhole logging instrument platforms, and the development of sufficiently fine spectral resolution Δλ in the miniaturization to facilitate discrimination between the variety of chemicals that may be encountered downhole in wellbore fluids.

A significant impediment for achieving high quality mid-IR (MIR) spectroscopy, as determined by spectral range, is the need for cooling of most detector technologies. Generally, uncooled detectors have limited responsivity in longer wavelength regimes, such as in the mid-IR range, for example, 250 wavenumbers ($cm^{-1}$) to 2000 $cm^{-1}$. Thus, as described herein, a detector formed using a metamaterial can provide the needed detectivity without cooling. The design of the metasurface may be adjusted or tuned to cover other spectral ranges, for example, by changing the size of the features in the pattern.

Theoretically, electromagnetic metamaterials can be designed to create arbitrary effective properties at any specific frequency by simply manipulating the design of special subwavelength resonator elements, or shapes, comprising the metamaterial geometric pattern. Accordingly, obtaining the desired properties in the metamaterial is a matter of development of the appropriate geometric elements for the frequency range and electromagnetic response of interest. As described herein, a metamaterial for infrared sensing is based upon thermal detection using arrays of very small thermal mass detector elements that interact with one or more electromagnetic modes. These are used to make broadband devices for spectroscopic chemical detection, which rely upon the tailored broadband characteristics of the metamaterial design.

In various embodiments described herein, the metamaterials are used in uncooled MIR microbolometer technologies in performance regimes currently occupied strictly by cryogenically cooled detector systems. Further, in various embodiments, the microbolometer detector 130 is incorporated into a miniaturized Michelson interferometer based on a micro-electromechanical system (MEMS), termed a MEMS interferometer 102, herein.

Figure 2:
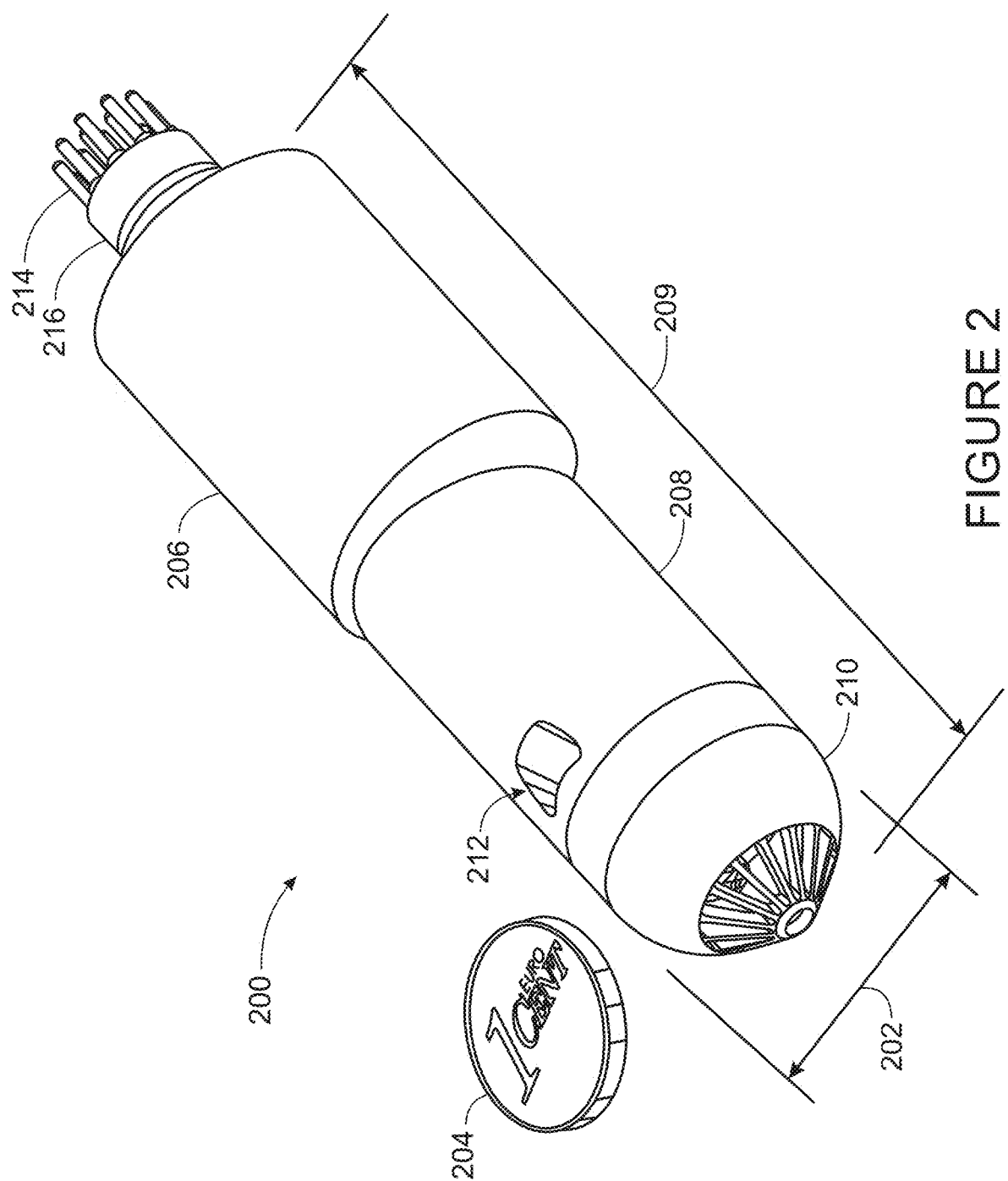
FIG. 2 is a perspective view of a miniature FT-MIR spectrometer (hereinafter FT-MIR), for example, for use in downhole applications.

FIG. 2 is a perspective view of a miniature FT-MIR spectrometer (FT-MIR) 200, for example, for use in downhole applications. As shown in FIG. 2, the FT-MIR 200 may have an outer diameter 202 of less than about 40 mm, or less than about 30 mm, or less than about 20 mm. In various embodiments, the outer diameter 202 is between about 15 mm and 20 mm at the sampling tip of the FT-MIR 200. As a comparison, a euro penny 204, with a diameter of about 16.25 mm, is illustrated in FIG. 2.

A pressure housing 206 supports the body 208 of the FT-MIR 200, for example, for mounting in a downhole measurement apparatus. The total length 209 of the FT-MIR 200 may be less than about 150 mm, or less than about 120 mm, or less than about 100 mm, or about 90 mm. The body 208 of the FT-MIR 200 couples to a flow-through shroud 210 that blocks debris from the well from damaging a sensor while allowing fluids to pass through an exit through a flow-through channel 212 on each side of the body 208. Electrical signals are exchanged with the FT-MIR 200 through electrical pins 214 mounted in a multi-pin feedthrough 216.

FIGS. 3A and 3B are side and top views of the FT-MIR 200 showing the path of wellbore fluids through the flow-through shroud 210. Like numbered items are as described with respect to FIG. 2. After passing through the flow-through shroud 210, the wellbore fluids contact a sampling surface of an attenuated total reflectance (ATR) prism 302, and then are directed out a flow-through channel 212 on each side of the FT-MIR 200. Wellbore flow streams may contain solids and particles that pose the risk of potential damage to the ATR prism sampling surface and must be filtered to reject particles larger than approximately 1.5 mm using a protective shroud forming a cavity requiring a flow-through design as illustrated in the plan and elevation views of FIG. 3A and FIG. 3B.

FIGS. 4A to 4D are different views of the flow-through shroud 210, showing dimensions that may be used in various embodiments. FIG. 4A is a perspective view of the flow-through shroud 210. FIG. 4B is a top view of the flow-through shroud 210. FIG. 4C is a side view of the flow-through shroud 210. FIG. 4D is a cut-away side view of the flow-through shroud 210.

As described herein, the flow-through shroud 210 shields the sampling surface of the ATR prism from solid particles in the downhole flow stream that may potentially damage the prism surface. In some embodiments, the flow-through shroud 210 prevents particles larger than 1 mm from impacting the sampling surface of the ATR prism, while allowing the wellbore fluid to quickly flow across the sampling surface and exit the prism chamber through the flow-through channels. This ensures that the fluid measured by the FT-MIR spectrometer corresponds to the surrounding fluid in the wellbore, allowing accurate fluid properties correlation with the depth position in the wellbore.

In some embodiments, the openings 402 are adjusted to exclude the expected solids to be found in the wellbore. For example, the openings 402 may be smaller for wellbores in which smaller particles, such as sand, are carried in the wellbore fluids. Larger openings 402 may be used in wellbores in which larger particles, such as drill cuttings, are carried in the wellbore fluids. In some embodiments, the flow-through shroud 210 is threaded to be detachable, allowing a different flow-through shroud 210, for example, with differently sized openings 402, to be attached to the body 208 (FIG. 2).

Figure 5:
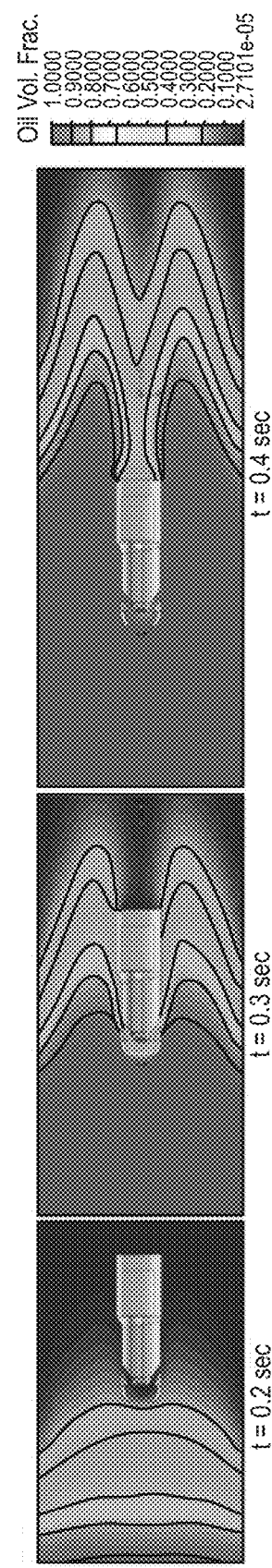
FIG. 5 shows contour plots of a simulation of the fluid flow dynamics for the probe showing the transition from water-to-oil.

FIG. 5 shows contour plots of a simulation of the fluid flow dynamics for the probe showing the transition from water-to-oil. The rate at which sampling is made affects the resolution of the downhole analysis logging operation, but the accuracy is substantially dependent upon the correlation of the fluid properties on the ATR sampling interface with the actual properties of the fluid surrounding the probe. The correlation quality is controlled by the sampling cavity design which affects the diversion and flow-through of the flow stream incident on the probe, and is a measure of the rapidity at which the fluid in the ATR sampling cavity exchanges, which is the design basis for the cavity flow-through geometry.

The lag time between fluid transition on the ATR sampling interface and that occurring in the surrounding wellbore fluid was evaluated from CFD simulation response using a notional scenario having a mean wellbore flow rate of 1 m/sec, initially comprised solely of fresh water then transitioning to a light crude oil very rapidly within 0.2 sec. As shown in FIG. 5, the water in the prism chamber, e.g., under the flow-through shroud, is replaced with oil within about 0.4 seconds, Resulting in 0.26 sec lag between the fluid transition in the wellbore and the fluid transition on the ATR sample surface.

Figure 6:
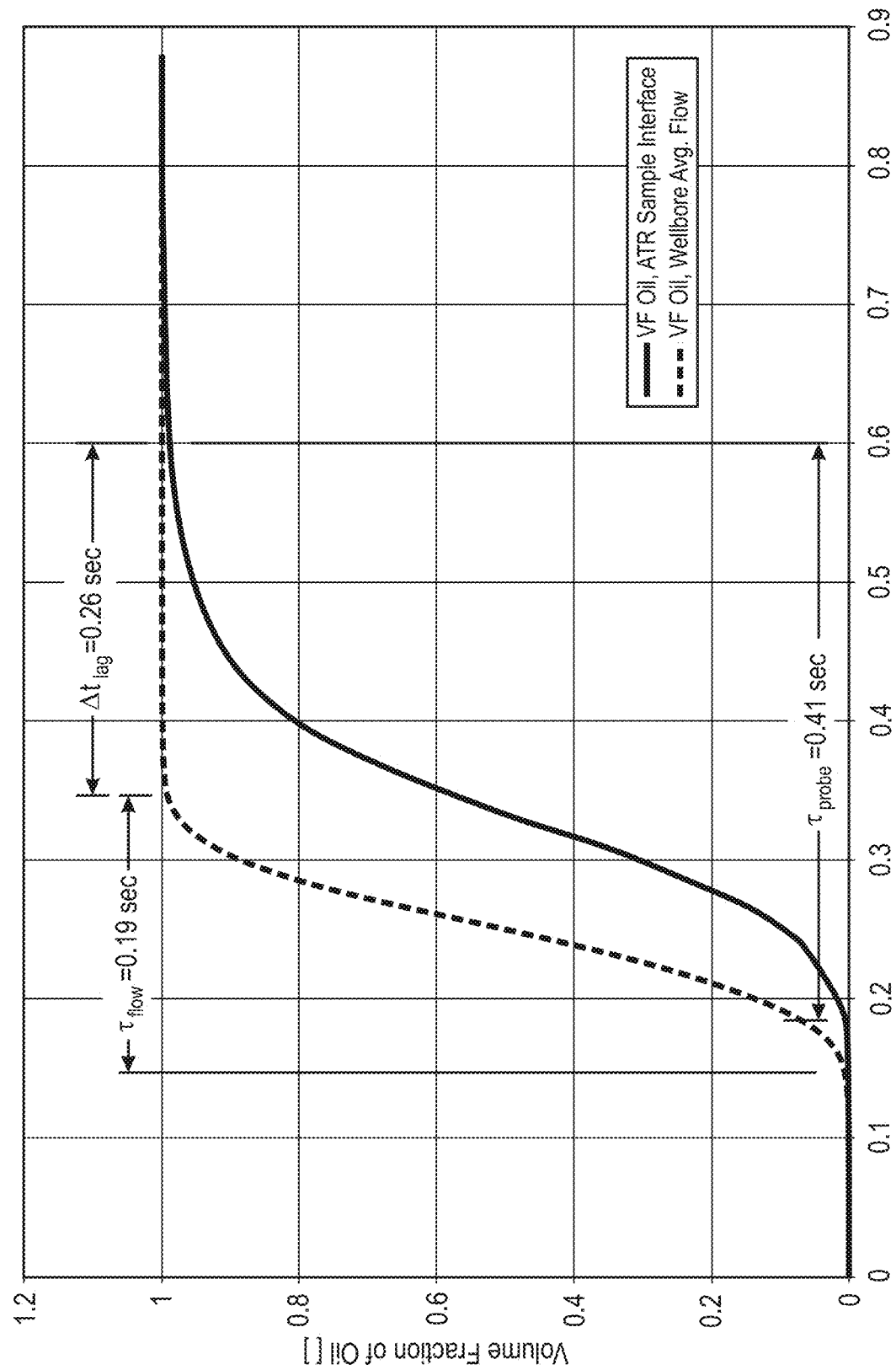
FIG. 6 is a plot of the transient response of the oil volume fraction on the ATR sampling surface and the average wellbore flow.

FIG. 6 is a plot of the transient response of the oil volume fraction on the ATR sampling surface and the average wellbore flow. The results indicate at the probe cross-section the transition time (99% oil volume fraction) for the wellbore flow $t_{flow}$=0.19 sec and the ATR sample interface transition time $t_{probe}$=0.41 sec, with approximately 0.26 sec differential in the time to reach 99% oil fraction. For this moderately rapid flow rate of 1 m/sec, 0.26 sec time differential for probe measurement lag is considered very acceptable for downhole real time measurement.

Figure 7:
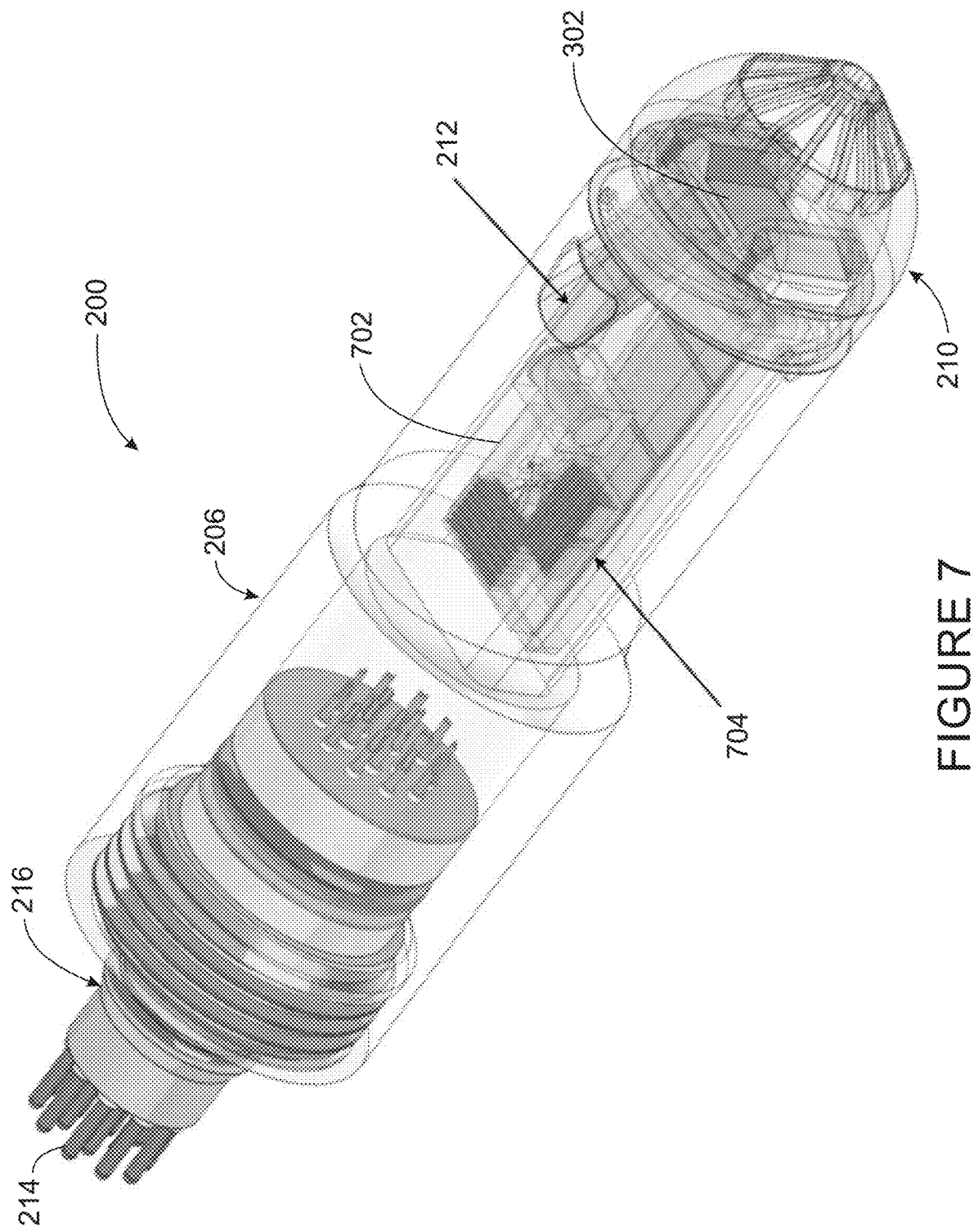
FIG. 7 is a transparent view of the FT-MIR showing the optical bench.

FIG. 7 is a transparent view of the FT-MIR 200 showing the optical bench 702. Like numbered items are as described with respect to FIG. 2. The optical bench 702 includes the optical components of the FT-MIR 200. The optical bench 702 is mounted on a Peltier thermal-control array 704, which is used to hold the temperature of the optical bench substantially constant, for example, at 40° C., 60° C., 80° C., or higher.

Figure 8A:
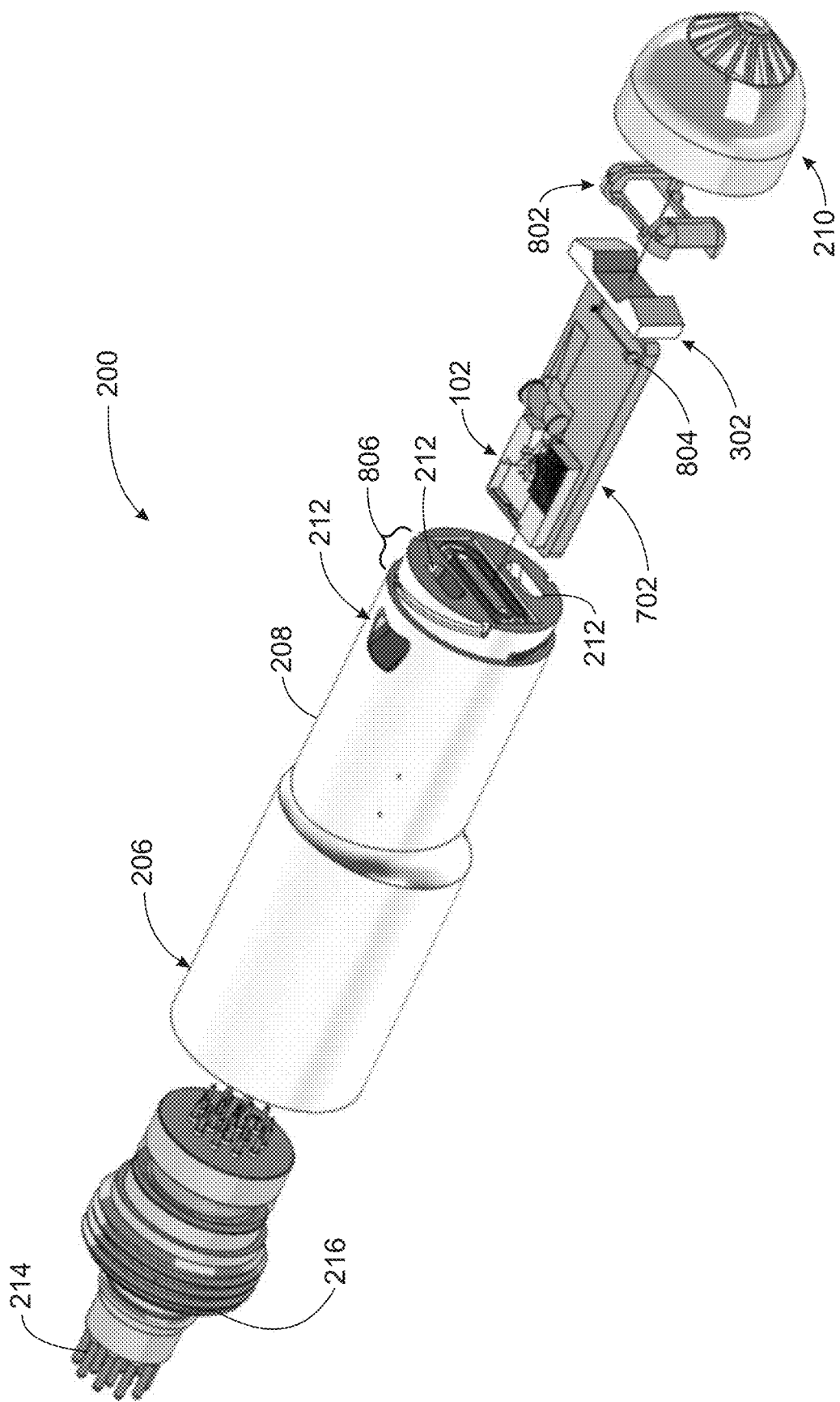
FIGS. 8A and 8B are exploded isometric views of the FT-MIR from two angles.
Figure 8B:
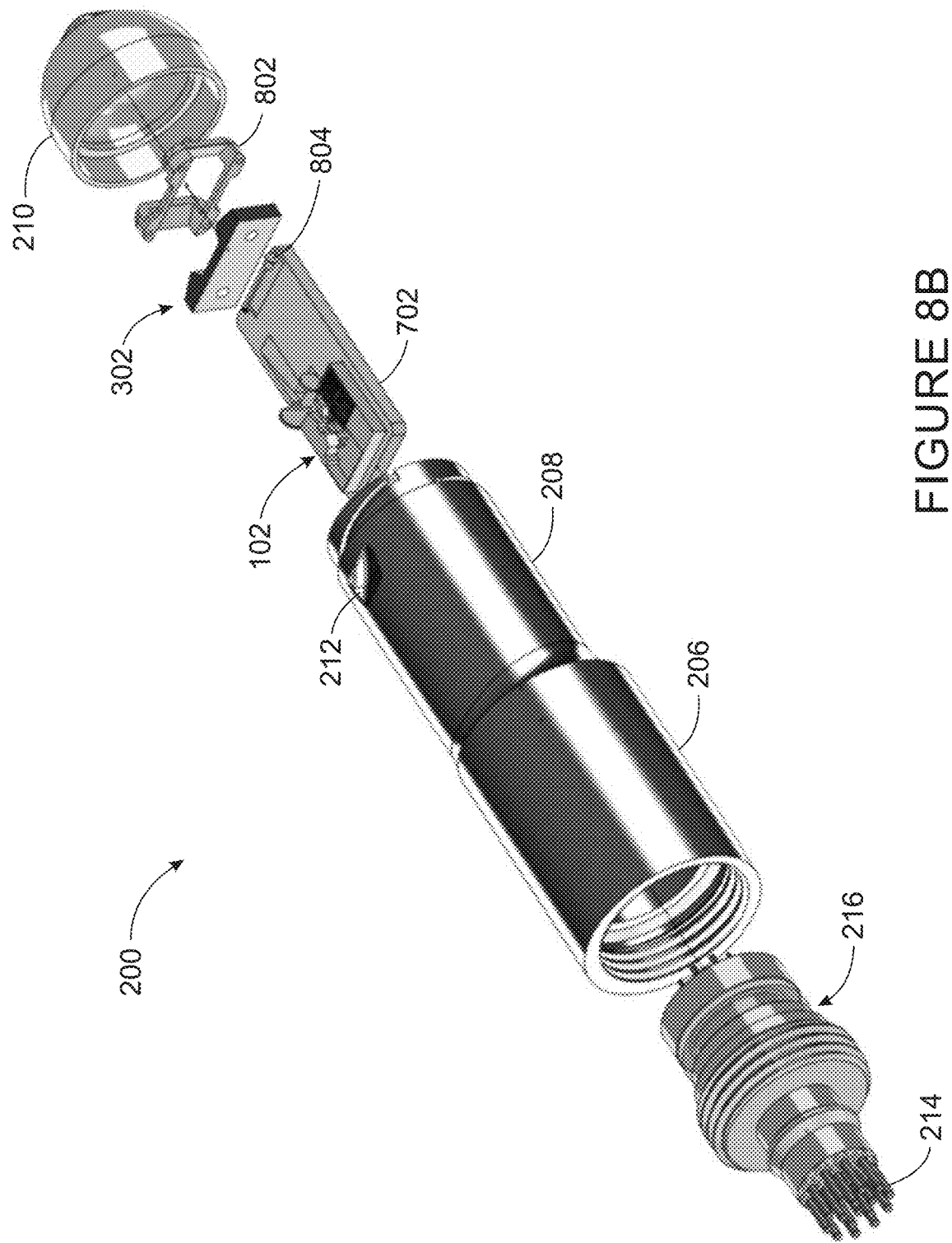
Figure 9:
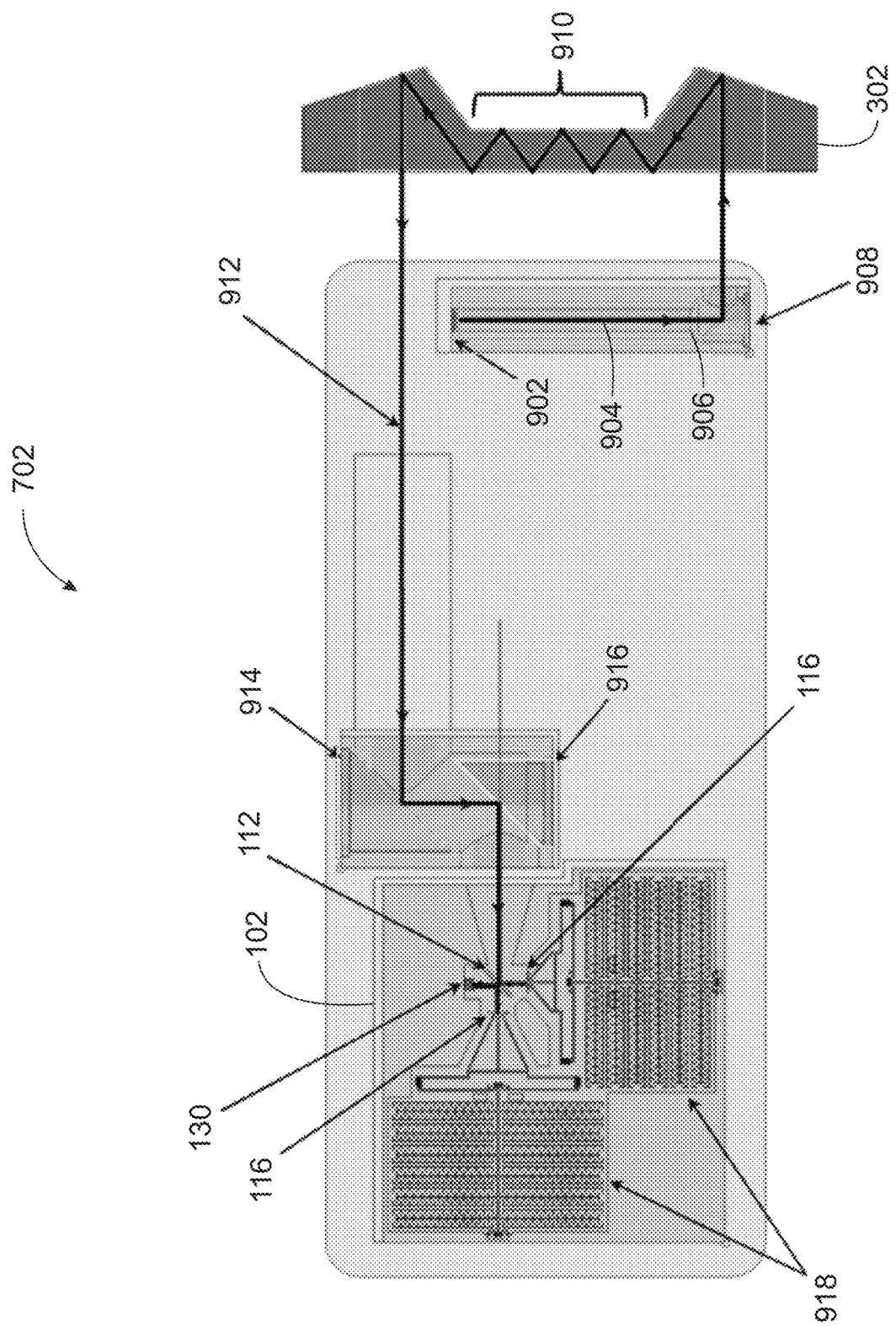
FIG. 9 is a schematic diagram of the gut-ray optical path on the optical bench of the FT-MIR (FIG. 2).

FIGS. 8A and 8B are exploded isometric views of the FT-MIR 200 from two angles. Like numbered items are as discussed with respect to previous figures. A prism retainer 802 holds the ATR prism 302 in place in the flow-through shroud 210. Both the metasurface IR source 804 and the MEMS interferometer 102 are mounted to the optical bench 702, forming a self-contained spectrometer. In some embodiments, a threaded region 806 on the body 208 of the FT-MIR 200 couples to the flow-through shroud 210 for assembly of the FT-MIR FIG. 9 is a schematic diagram of the gut-ray optical path on the optical bench 702 of the FT-MIR 200 (FIG. 2). Like numbered items are as described with respect to previous figures. The optical bench 702 includes an optical train that includes a near-zero index metasurface that is used as an infrared source 902. The metasurface is a 3×3 array of metasurface cells that are each 150 μm in size, and band-limited to the mid-infrared. The infrared source 902 emits the IR source beam 904 used for the measurement. The infrared source 902 is integrated directly in the millimeter-scale spectrometer enabling the miniaturization. A knife-edge baffle 906 is used to reduce the divergence of the IR source beam 904.

The IR source beam 904 is directed to the ATR prism 302 by an off-axis parabolic (OAP) mirror 908 for fluid sample interaction at a sampling surface 910, forming a sample beam 912. Off-axis-parabolic (OAP) mirrors 914 and 916 are used to focus and direct the sample beam 912 into the MEMS interferometer 102. In the MEMS interferometer 102, a pair of drive mechanisms 918 move the mirrors 116 to create the path-length differences. As each mirror 116 is moved in opposite directions, a longer path length difference is created. The resulting interferogram is measured using the integrated near-zero index metasurface, uncooled microbolometer detector 130. The miniaturization is possible due to the atypical physical properties obtained from the metasurface, which enable a micro-scale, perfect emitting infrared source 902 in combination with the uncooled perfect absorbing microbolometer detector 130.

In some embodiments, the miniature FT-MIR 200 fits within a 1500 mm$^3$ envelope, with an outer diameter of less than about 16 mm, which is compatible with a range of downhole application modes, including, for example, a multi-sensor array, production logging tool. As described herein, the miniature FT-MIR 200 can deliver a spectral resolution of 12 cm$^{-1}$ at a 1.5 Hz sampling rate over the mid-IR bandwidth 600-2000 cm$^{-1}$.

The optical train design performs the folding and focusing of the IR source beam 904 and sample beam 912 within the FT-MIR 200. The optical train configuration includes the OAP mirrors 908, 914, and 916. The OAP folding mirrors 908, 914, and 916 are selected to manipulate and converge the divergent source beam through the optical path to a focus on the microbolometer detector 130. The sample beam 912 is reduced to less than about 26% of the area of the initial baffled source beam 904 (about 0.196 mm$^2$ in a Ø0.5 mm, reduced down to about 0.052 mm$^2$ from an overlapping pair of eccentric beams of about Ø0.21 mm) resulting in about 75% minimum net intensity on the detector compared to the source baffle output. The miniature FT-MIR 200 was designed using a combination of detailed analysis techniques, which included finite element electromagnetic, finite element structural, and custom optical ray trace analyses. The optical ray trace analyses is discussed further with respect to FIG. 10.

Figure 10:
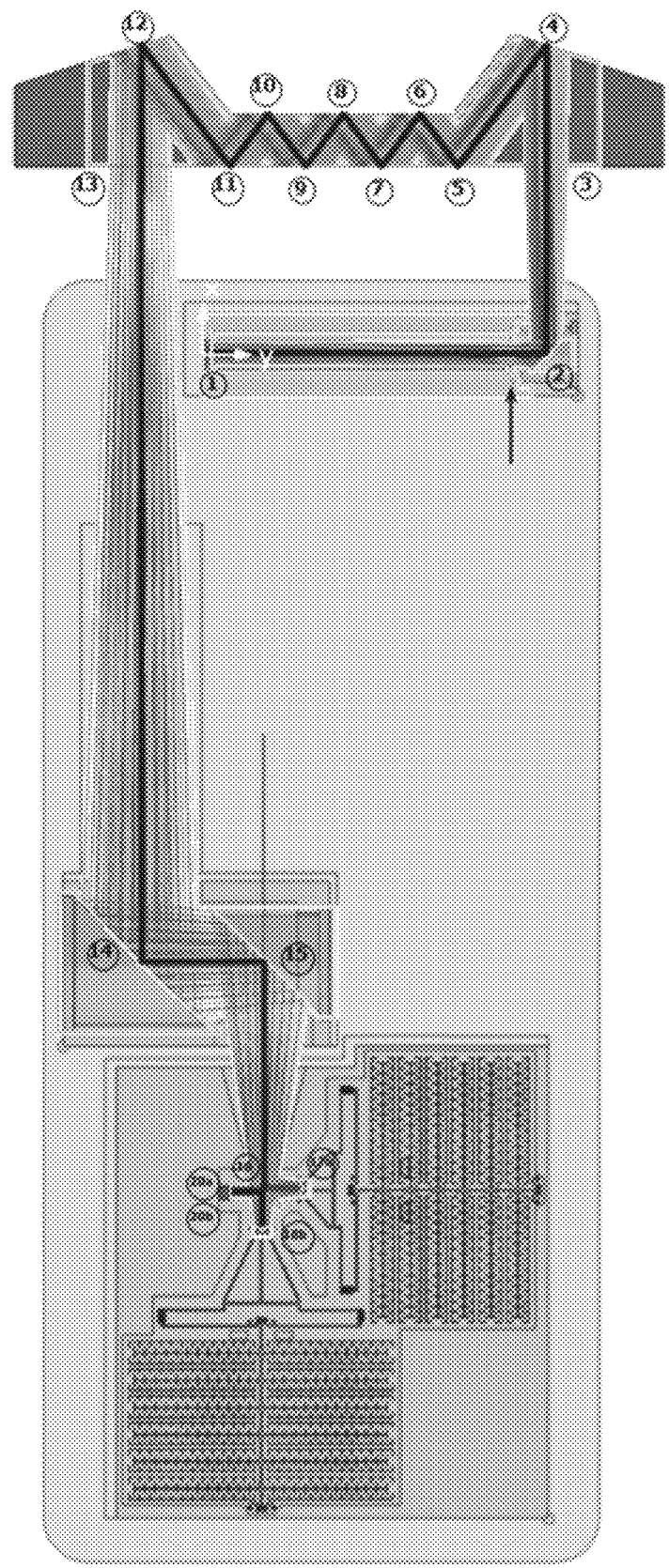
FIG. 10 is a drawing of an optical train ray trace analysis for the optical bench described in FIG. 9.

FIG. 10 is a drawing of an optical train ray trace analysis for the optical bench 702 described in FIG. 9. The optical ray trace analysis quantifies the beam divergence/convergence and transmission efficiency for the spectrometer for a set of mid-plane source points on the infrared metasurface emitter. A tabular listing of the gut-ray coordinates, beam diameter variation, and transmission throughput for the two moveable mirror paths is shown in Table 1. The main reflection points, corresponding to the items of Table 1, are annotated in FIG. 11, which correspond to the numbers in parenthesis, below.

The miniaturized optical train design is based on integrating the uncooled metasurface microbolometer with a MEMS based interferometer, germanium (Ge) ATR optical prism, and metasurface thermal infrared source within a compacted multiply-folded optical path as illustrated in FIG. 10. The radiation originates from the thermal infrared source at optical train location (1) as shown FIGS. 3A-3B. The metasurface thermal source is comprised of a 3×3 array of metasurface cells each 150 □m in diameter. The source radiation is directed along an optically black tube with the output aperture being defined by a single knife-edge baffle incident onto the first off-axis-parabolic (OAP) mirror at location (2) having a focal length F1=4.8 mm. The incident beam is folded by OAP-1 and incident onto the attenuated total reflection (ATR) prism at location (3) uncoated surface. The ATR prism has all surfaces reflectively coated excluding the sample interface surface at locations (6), (8), and (10) and the incident/exident diameters at location (3) and (13). The beam is folded by the reflectively coated chamfer surface at location (4) and directed onto the reflectively coated prism bottom surface at location (5). The design of the chamfer angle is chosen based upon the refractive indices of the prism material (Ge, n=4.0) and the expected fluid samples range (hydrocarbons, n=1.5-2.5) such that the beam incidence angle at locations (6), (8), and (10) ensures total reflection for the expected range of fluid sample refractive index with the only transmission loss being associated with evanescent wave propagation at the three reflection locations. The ATR prism uses a stepped thickness to produce three (3) total reflections at locations (6), (8), and (10) of an approximately ¬1.4 mm over a 5 mm length fluid sampling interface, which allows the total ATR prism length to be maintained less than 15 mm. The ATR prism output beam from location (13) is directed to a subsequent two-mirror fold-focus/fold-focus assembly at location (14) (OAP-2, F2=4.7 mm) and location (15) (OAP-3, F3=11.5 mm) then output onto the ZnSe 50/50 beamsplitter at location (16). Here the beam divides into two orthogonal paths of equal transmission: path-1 is created by a 50% reflection onto the moveable mirror MM1 at location (17a) and path-2 is created by a 50% transmission onto moveable mirror MM2 at location (18b). Each moveable mirror reflects the individual beams back onto the beamsplitter, with the path-1 having a 50% transmission and the path-2 having a 50% reflection finally onto the metasurface detector at locations (20a) and (20b).

Figure 12:
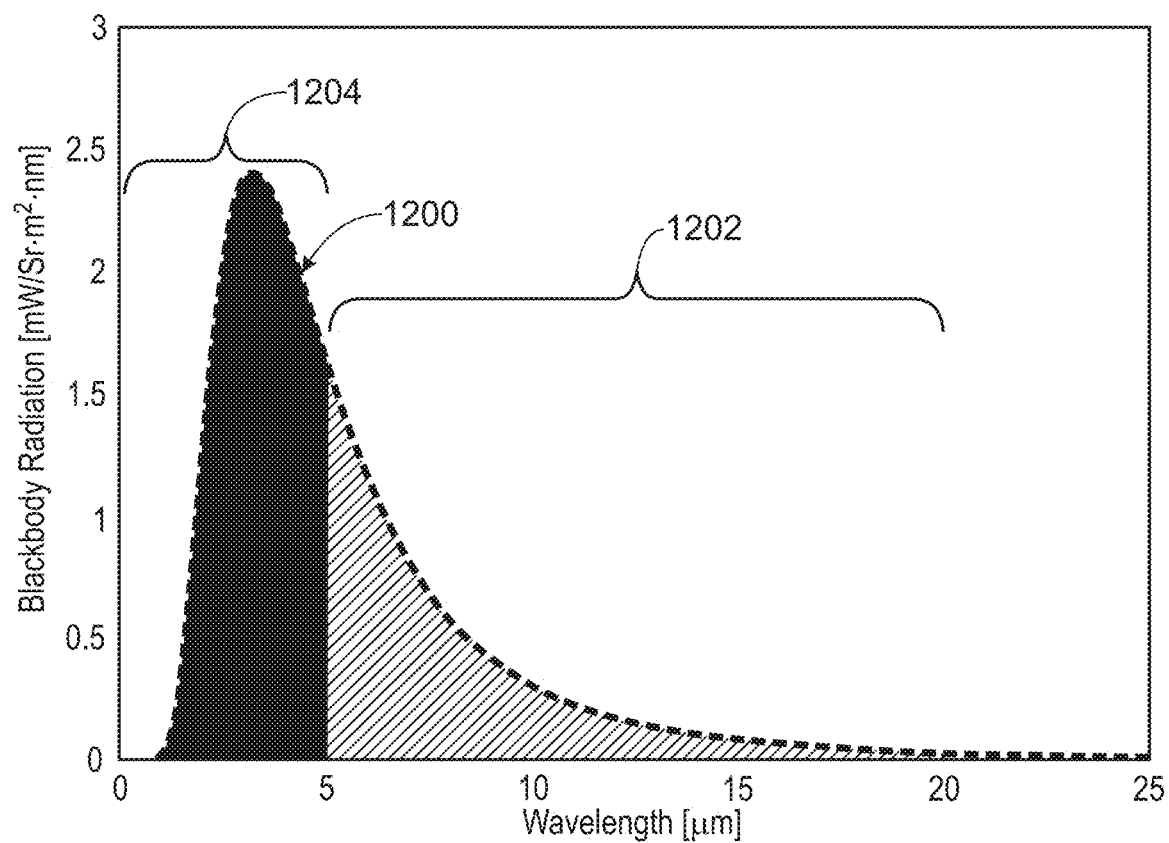
FIG. 12 is a plot of the black body radiation spectrum at 900 K indicating a mid-infrared bandwidth of interest for chemical spectroscopy.

FIG. 12 is a plot of the black body radiation spectrum 1200 at 900 K indicating a mid-infrared bandwidth of interest 1202 for chemical spectroscopy. In conventional infrared sources radiation is generated over very broad wavelength range, as shown by the black body radiation spectrum 1200, leading to the generation of significant waste heat 1204, which forms a thermal management problem for downhole application.

The mid-infrared source utilizes the unusual electromagnetic emittance properties of a metasurface design with a simple resistive heating filament that is embedded within a dielectric lamination. The resulting infrared radiation is confined primarily to the specific mid-infrared bandwidth of interest 1202 for downhole chemical spectroscopy. Thus, the excess heat problem is significantly reduced with the unusual bandwidth limited emittance properties of the metasurface.

The principle on which conventional infrared sources operate is based upon emittance over the classical Black-

TABLE 1

FT-MIR Optical train ray traces analysis. Tabular listing of gut-rays intersection coordinates and beam diameter change through optical train, units in millimeters.

| Path-1 | $Y_1$ | $X_1$ | $D_1$ | $TR_2$ | $IR_1$ | Path-2 | $Y_2$ | $X_2$ | $D_2$ | $TR_2$ | $IR_2$ |
|---|---|---|---|---|---|---|---|---|---|---|---|
| 1 | 0.00 | 0.00 | 0.50 | 1.00 | 100.0% | 1 | 0.00 | 0.00 | 0.50 | 1.00 | 100% |
| 2 | 7.63 | 0.00 | 0.62 | 1.00 | 64.7% | 2 | 7.63 | 0.00 | 0.62 | 1.00 | 64.7% |
| 3 | 7.63 | 4.30 | 0.94 | 0.64 | 18.0% | 3 | 7.63 | 4.30 | 0.94 | 0.64 | 18.0% |
| 4 | 7.63 | 7.09 | 1.00 | 0.64 | 16.1% | 4 | 7.63 | 7.09 | 1.00 | 0.64 | 16.1% |
| 5 | 5.61 | 4.30 | 1.31 | 0.64 | 9.3% | 5 | 5.61 | 4.30 | 1.31 | 0.64 | 9.3% |
| 6 | 4.74 | 5.50 | 1.35 | 0.64 | 8.8% | 6 | 4.74 | 5.50 | 1.35 | 0.64 | 8.8% |
| 7 | 3.86 | 4.30 | 1.38 | 0.64 | 8.4% | 7 | 3.86 | 4.30 | 1.38 | 0.64 | 8.4% |
| 8 | 2.99 | 5.50 | 1.42 | 0.64 | 8.0% | 8 | 2.99 | 5.50 | 1.42 | 0.64 | 8.0% |
| 9 | 2.12 | 4.30 | 1.45 | 0.64 | 7.6% | 9 | 2.12 | 4.30 | 1.45 | 0.64 | 7.6% |
| 10 | 1.25 | 5.50 | 1.48 | 0.64 | 7.3% | 10 | 1.25 | 5.50 | 1.48 | 0.64 | 7.3% |
| 11 | 0.38 | 4.30 | 1.52 | 0.64 | 6.9% | 11 | 0.38 | 4.30 | 1.52 | 0.64 | 6.9% |
| 12 | −1.65 | 7.09 | 1.29 | 0.64 | 9.6% | 12 | −1.65 | 7.09 | 1.29 | 0.64 | 9.6% |
| 13 | −1.65 | 4.30 | 1.35 | 0.64 | 5.7% | 13 | −1.65 | 4.30 | 1.35 | 0.41 | 5.7% |
| 14 | −1.65 | −14.00 | 2.71 | 0.41 | 1.4% | 14 | −1.65 | −14.00 | 2.71 | 0.41 | 1.4% |
| 15 | 1.15 | −14.00 | 2.14 | 0.41 | 2.2% | 15 | 1.15 | −14.00 | 2.14 | 0.41 | 2.2% |
| 16 | 1.15 | −19.20 | 0.53 | 0.20 | 18.6% | 16 | 1.15 | −19.20 | 0.53 | 0.20 | 18.6% |
| 17a | 1.94 | −19.20 | 0.29 | 0.20 | 62.6% | 17b | 1.10 | −19.29 | 0.52 | 0.20 | 19.1% |
| 18a | 1.15 | −19.20 | 0.23 | 0.10 | 50.2% | 18b | 1.10 | −20.06 | 0.28 | 0.20 | 63.1% |
| 19a | 1.06 | −19.25 | 0.22 | 0.10 | 50.9% | 19b | 1.10 | −19.29 | 0.23 | 0.10 | 49.7% |
| 20a | 0.40 | −19.25 | 0.18 | 0.10 | 75.3% | 20b | 0.40 | −19.29 | 0.18 | 0.10 | 75.3% |

Figure 11:
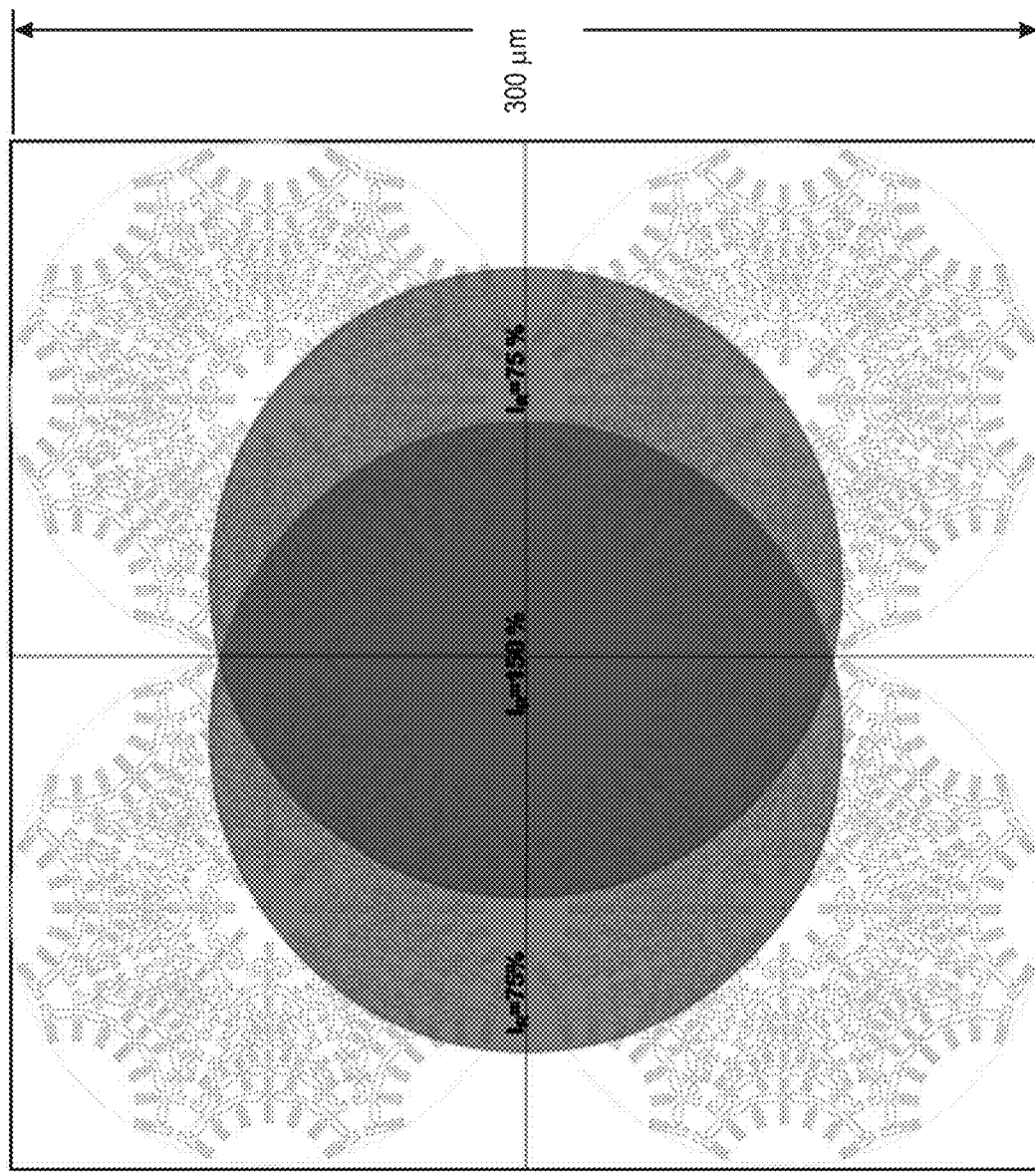
FIG. 11 is a drawing of the beam spot geometry on the uncooled microbolometer detector that is comprised of a 2×2 array of metasurface cells of the same geometry as the thermal infrared source cells.

FIG. 11 is a drawing of the uncooled microbolometer detector, which is comprised of a 2×2 array of metasurface cells of the same geometry as the thermal infrared source cells. The two beams recombine on the metasurface detector at locations (20a) and (20b) in FIG. 10, with a footprint formed by two eccentric circles as illustrated in FIG. 11, fitting within an oval-shaped envelope 0.184 mm×0.228 mm. Due to the eccentricity of the two beams the detector spot pattern is comprised of a non-uniform intensity central double-crescent with 150% net intensity signal and two single-crescent side-lobes with 75% net intensity each. The central double-crescent and the two single-crescent side-lobes have approximately equal areas. This results in about 54% of the detector spot pattern area having 150% net relative intensity (~1000 mW/cm$^2$), and the remainder comprised in the side-lobes with 75% net relative intensity. A graphical summary of the spectrometer design is illustrated in FIG. 10 for a set of mid-plane emittance points on the infrared metasurface source, with the gut-ray coordinates, beam diameter variation, and intensity throughput for the two moveable mirror paths shown in the tabular listing in Table 1.

body radiation spectra 1200. The intended infrared energy level within the wavelength range of interest is generated simply by controlling the temperature of an emitting surface and the radiation in wavelengths outside the bandwidth of interest constitutes excess waste heat that must be managed by the optical bench thermal design. The Blackbody radiation spectrum 1200 from the emitter is intrinsically concentrated over the visible and near infrared wavelength ranges. For mid-infrared spectroscopy applications in downhole chemical analysis, we are interested in the electromagnetic wavelength range 5-20 μm (2000-500 cm$^{-1}$). However, the predominant portion of Blackbody radiation lies outside this bandwidth below 5 μm wavelength, which is unusable waste heat 1204 and creates a heat source problem that significantly influences the design of the infrared source assembly.

As an illustration, consider the Blackbody radiation spectrum 1200 shown in FIG. 12, corresponding to a radiating blackbody at 900 K. The spectrum shows that the energy radiated by the body in the wavelength range below about 5 μm (2000 cm$^{-1}$) is greater than the energy in the wavelength larger than 5 μm, in fact comprising about 60% of the total radiation. This is a waste heat load that would need to be managed by the spectrometer design. This is one of the practical obstacles confronting MEMS scale miniaturization of laboratory quality spectroscopy instruments.

Figure 13A:
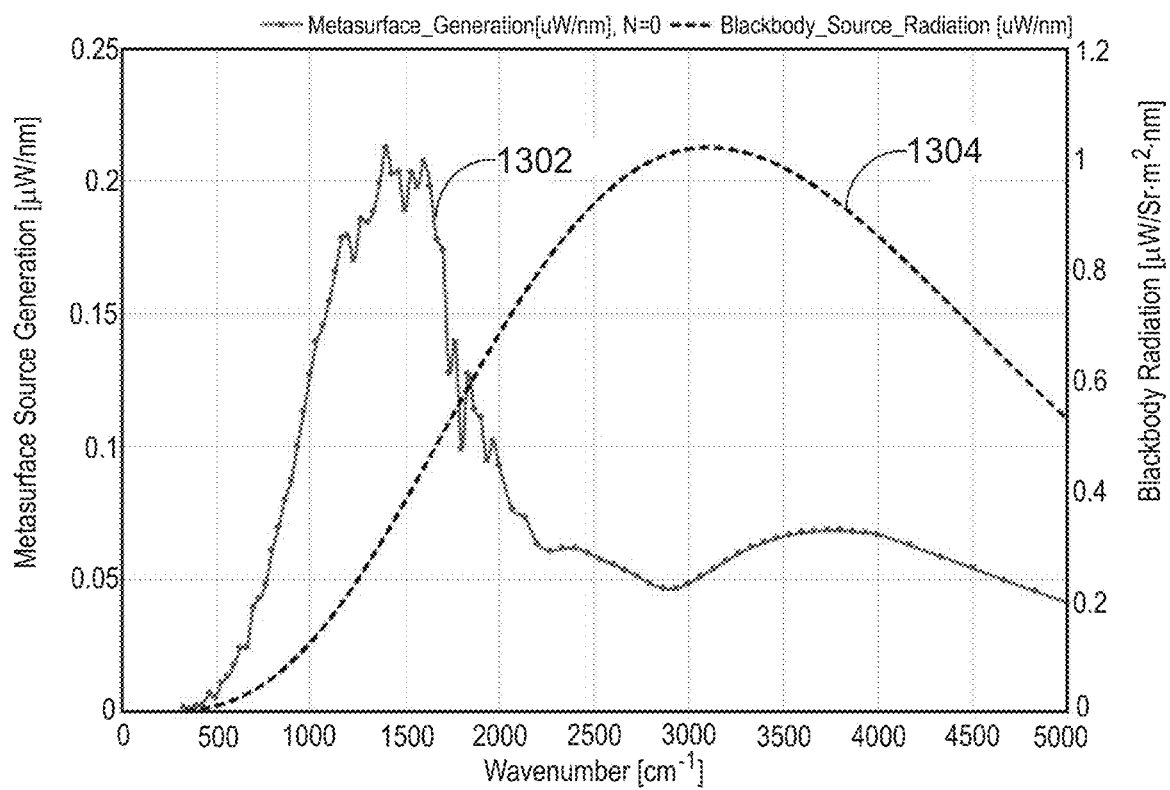
FIGS. 13A and 13B are plots of electromagnetic spectra comparing the blackbody radiation at 900 K to the emittance spectrum of the metasurface source, and absorption spectra for crude oil samples from various regions.
Figure 13B:
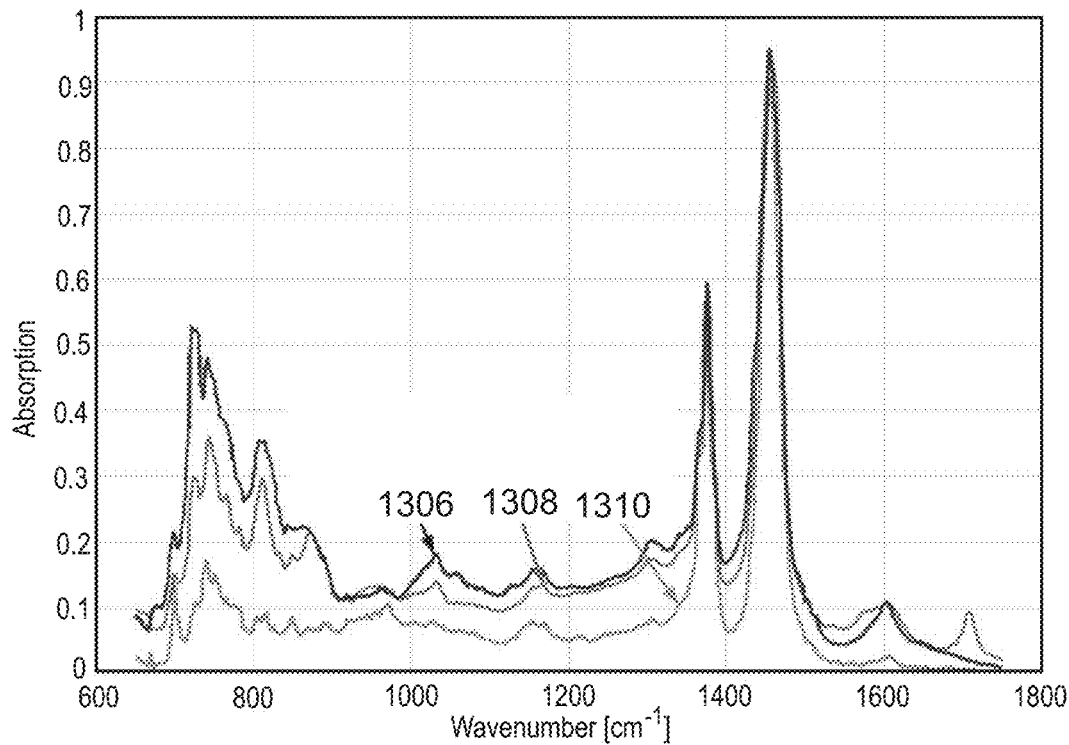

FIGS. 13A and 13B are plots of electromagnetic spectra comparing the blackbody radiation at 900 K and the metasurface source radiation, to absorption spectra for crude oil samples from various regions. The properties of the metasurface perfect absorber can be used to create a bandwidth-limited infrared source that radiates more energy in the mid-IR. For an arbitrary body emitting and absorbing thermal radiation in thermodynamic equilibrium, the absorptivity and emissivity are equivalent. Thus, the bandwidth-limited perfect absorptivity characteristics of the metasurface translate into bandwidth-limited perfect emissivity characteristics as well.

This concept is illustrated in FIG. 13A, which depicts a comparison of the radiation spectrum 1302 from a 3×3 array of the metasurface cells imprinted onto a $Si_3N_4$ substrate controlled to 900 K and the natural Blackbody radiation spectrum 1304 for 900 K. The comparison in the figure indicates that the bulk of the waste heat problem is eliminated by the bandwidth-limited emissivity of the metasurface array, with the electromagnetic radiation concentrated within the wavenumber range about 2000-500 $cm^{-1}$ (5-20 μm) being of specific interest for the downhole chemical analysis application as highlighted in the crude oil absorption spectra shown in FIG. 13B. The SARA fractions (saturate, aromatic, resin, and asphaltene) for the crude oil samples in FIG. 13B are summarized in Table 2.

TABLE 2

SARA fractions of three crude oil samples

| Origin | Saturates (wt. %) | Aromatics (wt. %) | Resins (wt. %) | Asphaltenes (wt. %) | Density (g/cc) | Reference Number |
|---|---|---|---|---|---|---|
| North Sea | 82.7 | 13.4 | 3.9 | 0 | 0.839 | 1306 |
| West Africa | 42.4 | 36.1 | 20.5 | 1 | 0.921 | 1308 |
| France | 24.2 | 43.4 | 19.9 | 12.4 | 0.939 | 1310 |

Figures 14A, 14B:
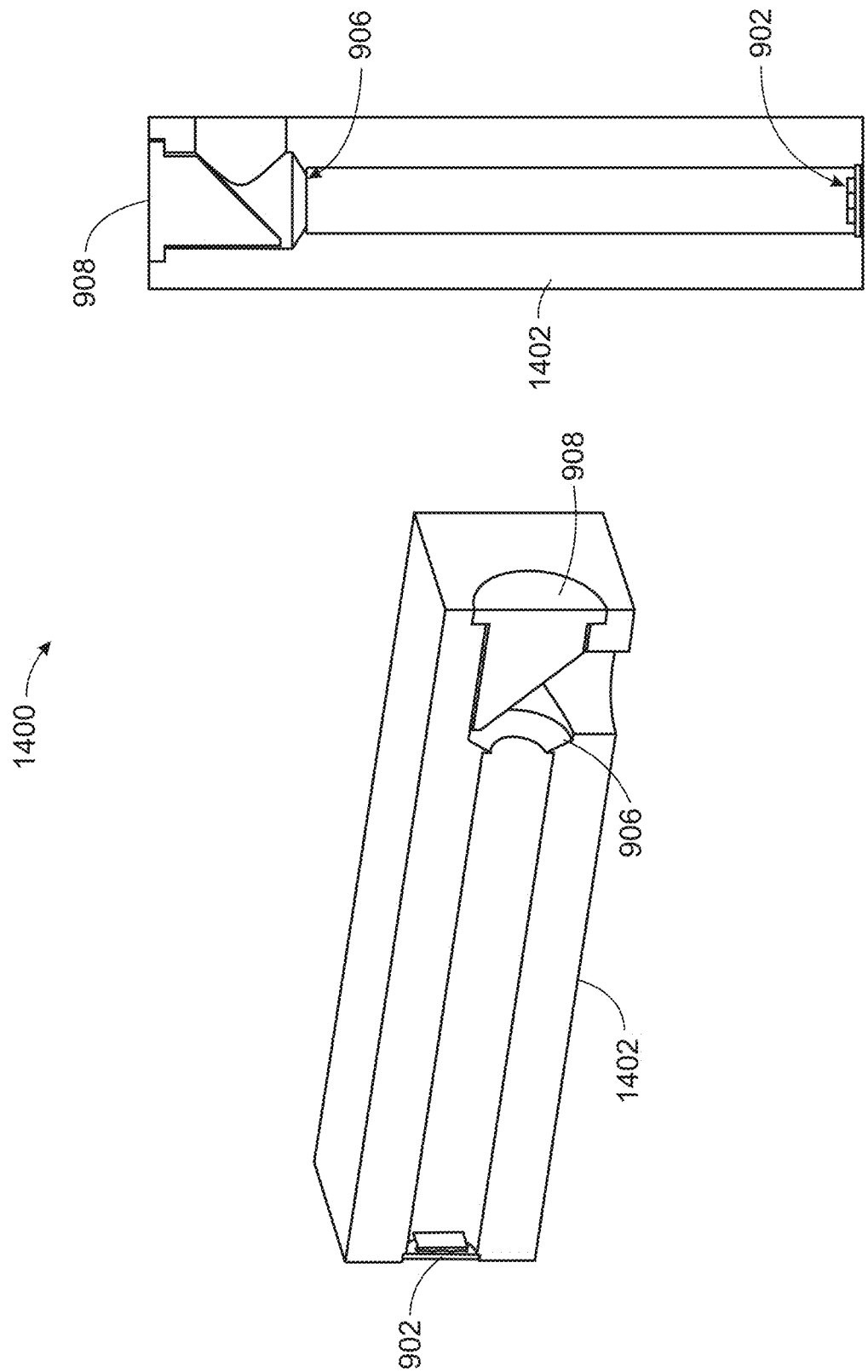
FIGS. 14A and 14B are drawings of an infrared source module using the metasurface IR source.

FIGS. 14A and 14B are drawings of an infrared source module 1400 using the IR source 902. Like numbered items are as described with respect to FIG. 9. The metasurface infrared source module 1400 includes the metasurface IR source 902, an off-axis-parabolic (OAP) folding mirror 908, and an optical-tube 1402, which houses the two optical components and creates the knife-edge baffle 906 that decreases the divergence of the incidence beam onto the OAP mirror 908. The IR source 902 uses an array of metasurfaces, as discussed with respect to FIG. 15. The design of the heating filament for the emitter is discussed with respect to FIGS. 16A and 16B. The target temperature of the source array is maintained by controlling the electrical current in the heating filament through a pulse-width-modulation scheme on the electrical voltage across the filament.

Figure 15:
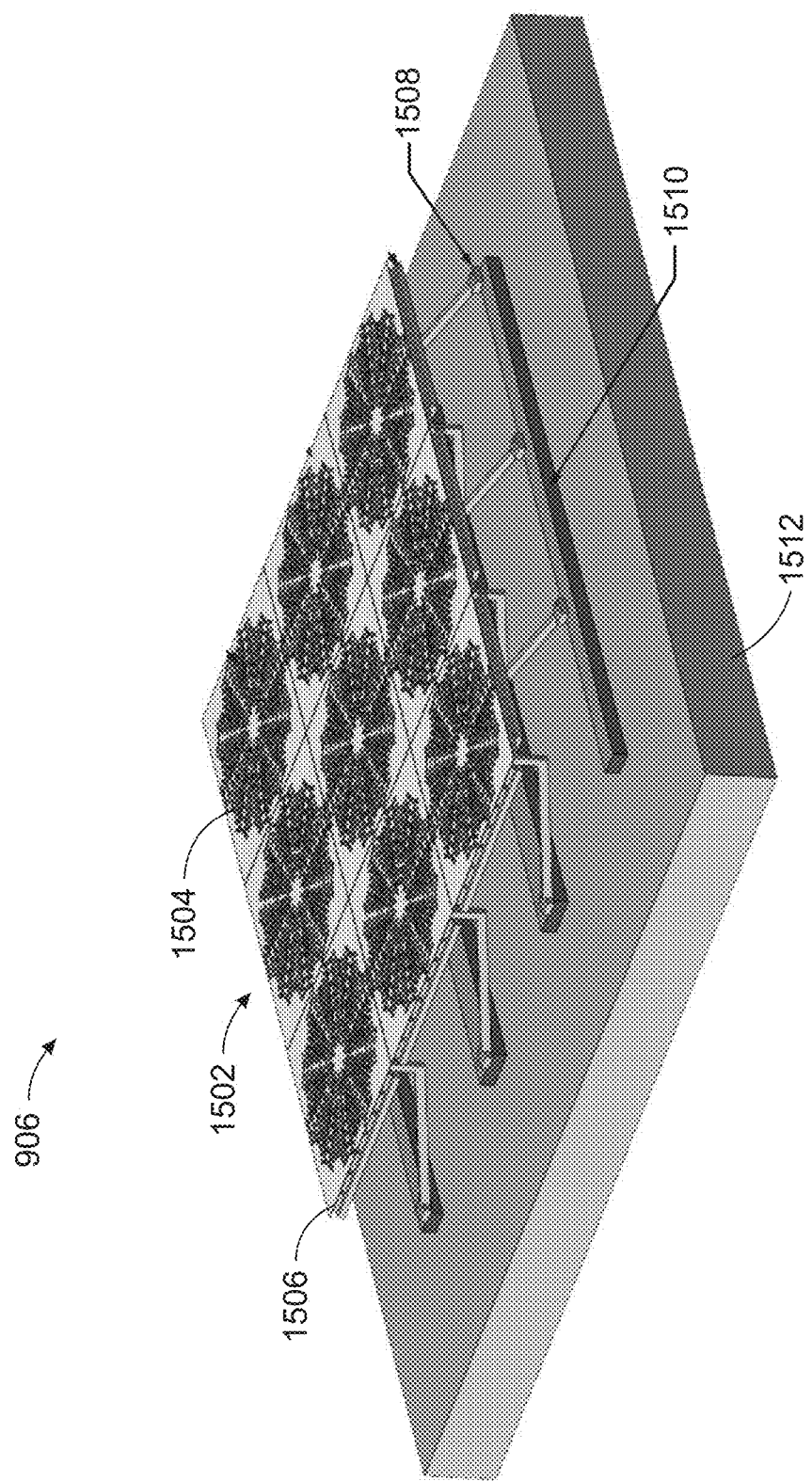
FIG. 15 is a drawing of the IR source showing an array of metasurface emitters.

FIG. 15 is a drawing of the IR source 902 showing an array 1502 of metasurface emitters 1504. The top surface of a dielectric lamination 1506 is imprinted with a 3×3 array of the metasurface emitters 1504. As described herein, the metasurface is tuned to behave as a perfect absorber within a defined mid-infrared bandwidth. From Kirchhoff's law, the perfect absorption of the metasurface translates into perfect emittance characteristics within the same definitive mid-infrared bandwidth. This physical property of the metasurface therefore creates a bandwidth limited filter on the inherent Blackbody radiation of the dielectric lamination so that the device emits the predominant portion of energy within the mid-infrared range of interest for investigating the fingerprint region corresponding to a variety of hydrocarbon compositions.

A resistive heating filament, as discussed with respect to FIGS. 16A and 16B is embedded within the dielectric lamination 1506. The heating filament is coupled through contacts 1508 to electrical busbars 1510 on a support substrate 1512.

FIGS. 16A and 16B are drawings of the heating filament 1602 for the metasurface source array 906 of FIG. 15. The electrical current in the heating filament 1602 is controlled to stabilize the temperature of the dielectric lamination to 600° C., which normally emits with a specific Blackbody radiation spectrum in which the predominant portion of the output energy is generated within the near-infrared and visible wavelength ranges. The heating filament 1602 is disposed over the dielectric substrate 1506, and is powered by contact legs 1604, which also provide thermal isolation designed to promote microbolometer sensitivity.

Figure 17A:
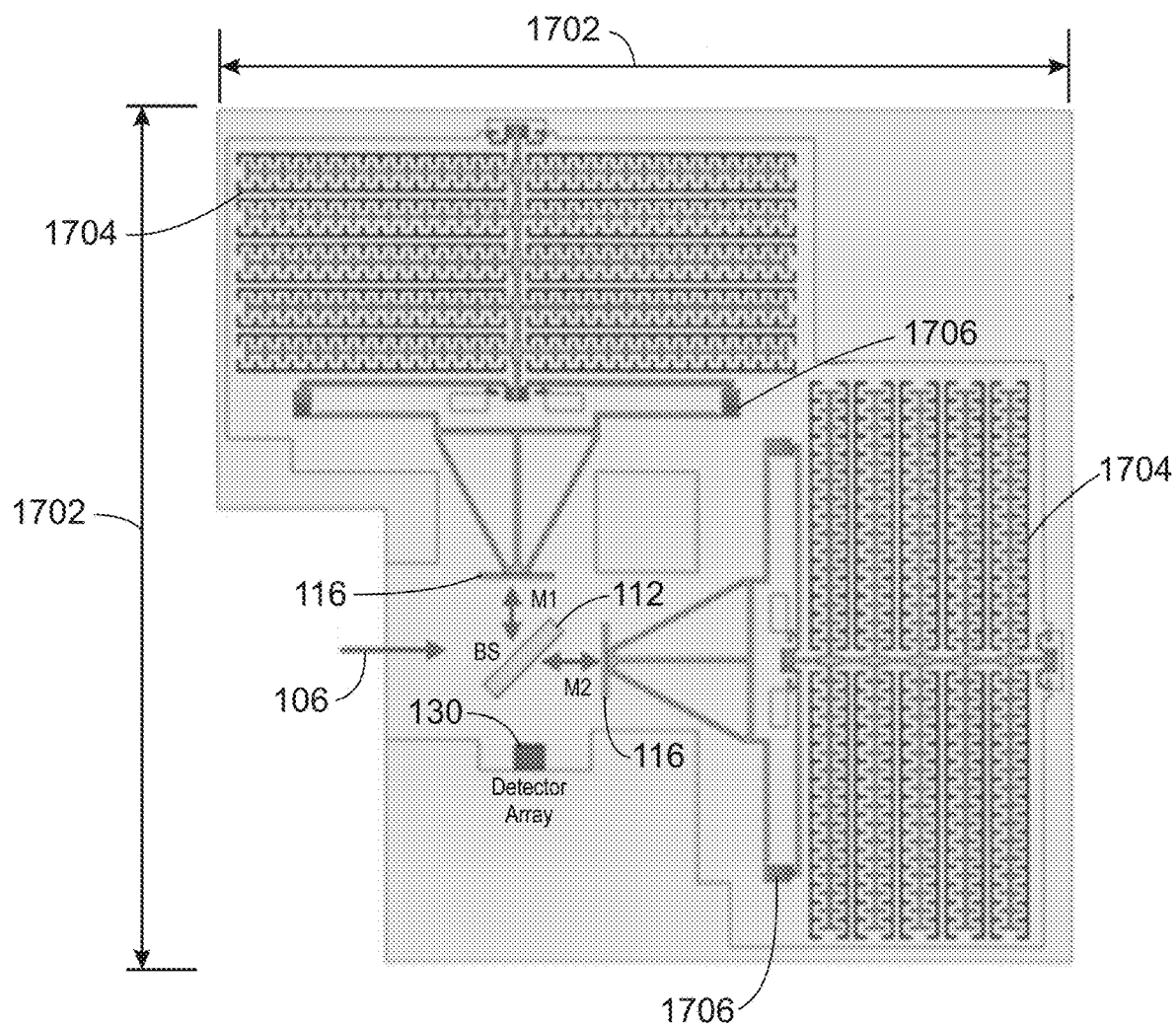
FIGS. 17A and 17B are schematic diagrams of a micro-electromechanical system (MEMS) interferometer for the FT-MIR.
Figure 17B:
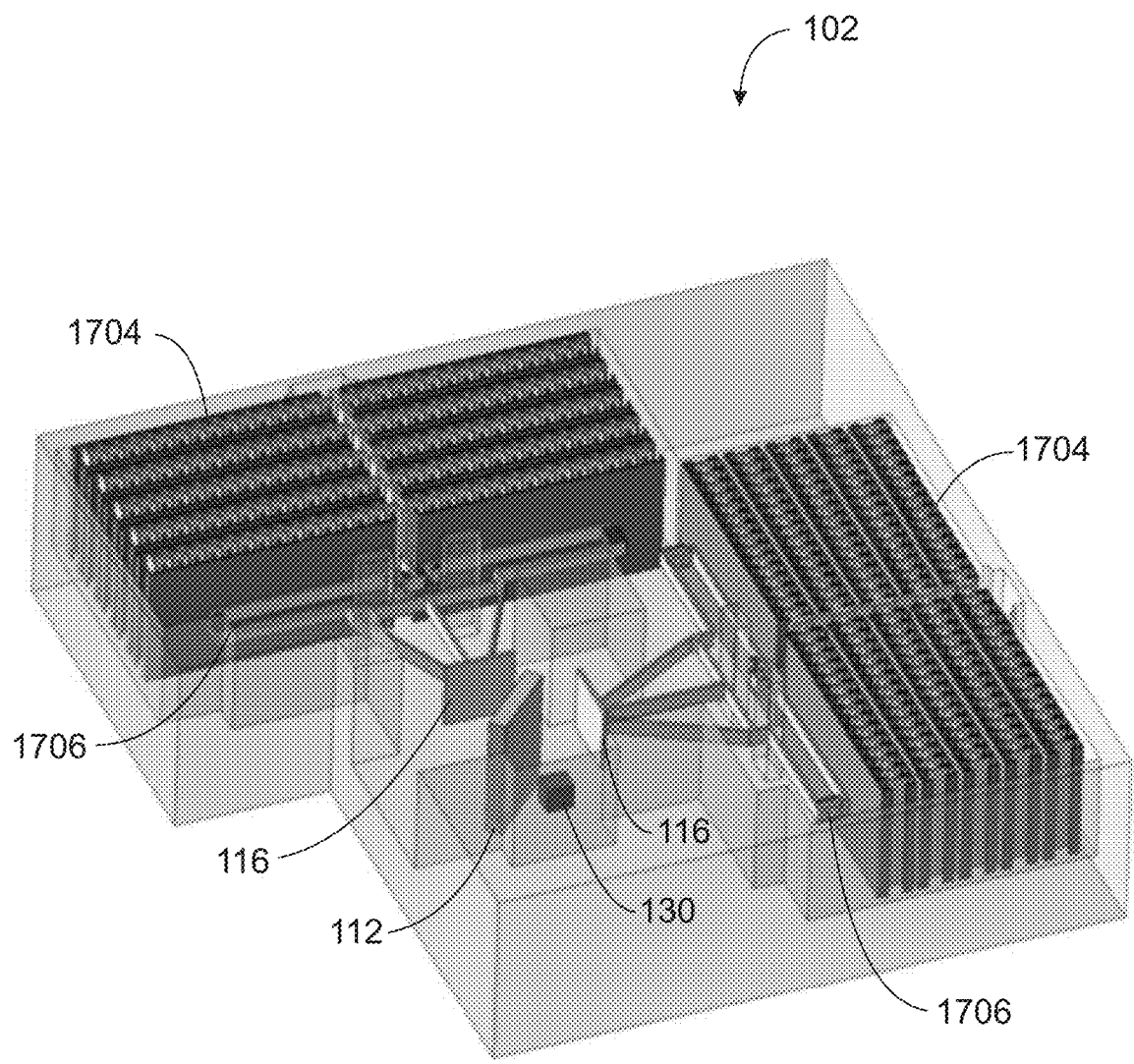

FIGS. 17A and 17B are schematic diagrams of a microelectromechanical system (MEMS) interferometer 102 for the FT-MIR. Like numbered items are as described with respect to FIG. 1. FIG. 17A is a top view of the MEMS interferometer 102, while FIG. 17B is a perspective view of the MEMS interferometer 102. In various embodiments, the MEMS interferometer 102 is formed into a single monolithic chip or block of substrate, with dimensions 1702 of about 9.5 mm×9.5 mm.

As described herein, in various embodiments the FTIR MIR spectrometer is based on a metasurface microbolometer, used as the detector 130, which exhibits good absorption in the biological fingerprint region of the electromagnetic spectrum, e.g., from about 500 $cm^{-1}$ to about 2000 $cm^{-1}$. This region is useful for identifying and analyzing many hydrocarbons and wellbore fluids. The MEMS interferometer 102 utilizes a pair of mechanisms that drive movable micromirrors, or mirrors 116. Each mechanism includes an electrostatic actuator 1704 on the chip that drives a mirror 116 through a displacement amplification mechanism 1706. Each mirror 116 is placed along a perpendicular axis extending through a beamsplitter 112. The input beam 106 is divided by the beamsplitter 112 and sent to each mirror 116, then recombined to create constructive and destructive interference in a beam from the beamsplitter 112 to the detector 130. As described herein, in various embodiments the detector 130 is a metasurface detector that does not require cryogenic cooling.

The displacement amplification mechanism 1706 increases the spectral resolution of the MEMS interferometer 102 by increasing the amplitude of the motion of each mirror 116. The displacement amplification mechanism 1706 increases the motion of each mirror 116 by a ratio of about 9.4:1 over the input motion from the electrostatic actuator 1704. This is described in further detail for a single mechanism with respect to FIGS. 18A and 18B.

Figure 18A:
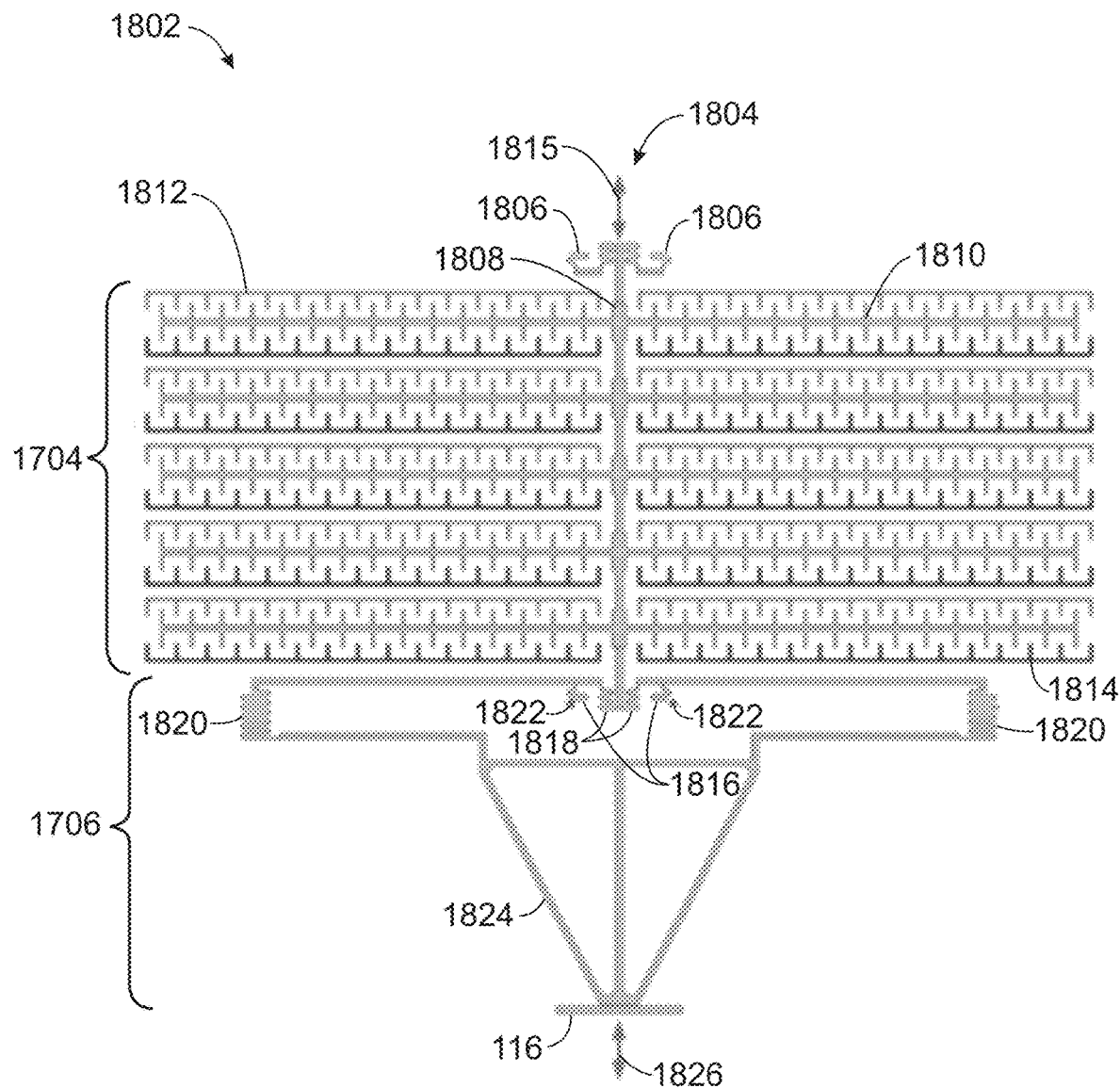
FIGS. 18A and 18B are cross-sections of the mechanism used for moving each mirror in the MEMS interferometer.
Figure 18B:
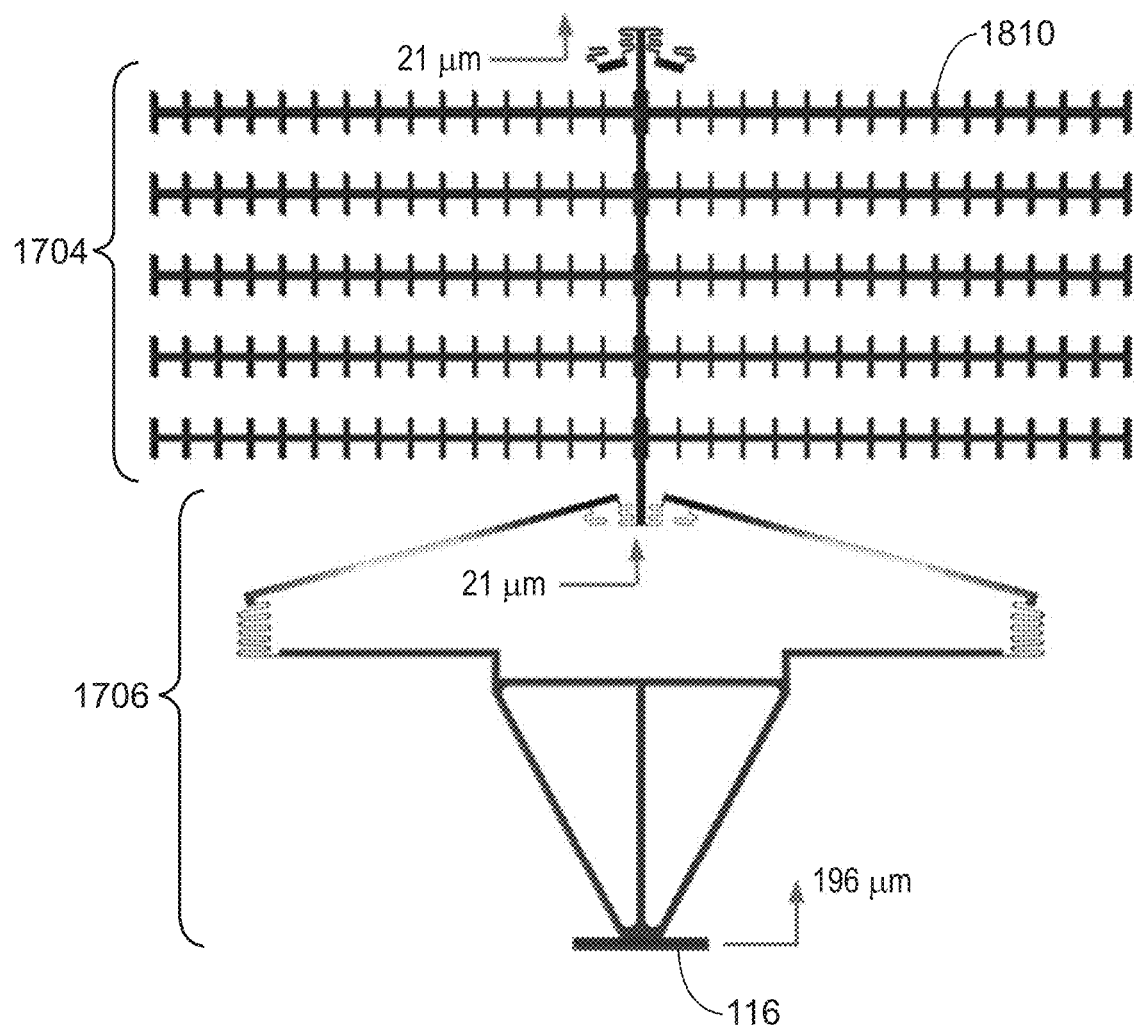

FIGS. 18A and 18B are cross-sections of the mechanism used for moving each mirror 116 in the MEMS interferometer 102. Like numbers are as described with respect to FIGS. 1, 17A and 17B. Each mirror 116 is controlled by a coupled electrostatic actuator 1704 that uses a comb drive mechanism 1802.

The motion of the electrostatic actuator 1704 drives the displacement amplification mechanism 1706. The comb drive mechanism 1802 includes a sway stabilizer 1804 that is attached to the substrate at two attachment points 1806. As described herein, the sway stabilizer 1804 assists in keeping the motion of the comb drive mechanism 1802 linear at high drive voltages. The comb drive mechanism 1802 includes a central actuator 1808 that is attached to movable combs 1810 that has grounded tines that are positioned between tines extending from positive combs 1812 (positive tines) and negative combs 1814 (negative tines), which are fixed in place. Each tine from the movable comb 1810 is positioned about 70 µm from a tine on one of the other combs 1812 or 1814. Applying a voltage potential between the positive combs 1812 and the negative combs 1814 will cause the movable combs 1810 to oscillate between the positive combs 1812 and the negative combs 1814, moving the central actuator 1808. The amplitude of the motion 1815 is proportional to the potential difference between the positive combs 1812 and the negative combs 1814.

As described herein, the displacement amplification mechanism 1706 amplifies the motion, $\Delta_{Act}$, of the comb drive mechanism 1802 to increase the total displacement of the mirror 116 $\Delta_{Mirr}$ 1826. The displacement amplification is created through the combination of a symmetric fulcrum about the axis of the central actuator 1808 and three pairs of serpentine moment release flexures 1816, 1818, and 1820. The comb drive mechanism 1802 imparts motion on the central actuator 1808, which activates the fulcrum lever about the constraint, or attachment, points 1822 resulting in an amplification of the actuator motion 1815 at the mirror 116 (motion 1826). The three pairs of serpentine moment release flexures 1816, 1818, and 1820 are designed to function as quasi-perfect hinge joints at each location. The degree of departure from the perfect hinge moment release degrades the mirror and actuator amplification ratio of the motion 1826 of the mirror 116. For the idealized case in which the three pairs of serpentine release flexures 1816, 1818, and 1820 could be replaced by perfect ball-joints, the amplification ratio would be approximately 10:1 whereas in the practical design case involving the serpentine release flexures 1816, 1818, and 1820 as built, the amplification ratio of the motion 1815 of the central actuator 1808 to the final motion 1826 of the mirror 116 is about 9.4:1, due to the incomplete release of the moment constraints.

The sway stabilizer 1804 allows an increase in the vibrational loading at which the comb drive mechanism 1802 experiences lateral instability. The sway stabilization 1804 mechanism is integrated at the extreme location of the central actuator 1808 from the displacement amplification mechanism 1706.

FIG. 18B is a schematic diagram of the motion of the mirror 116. As illustrated FIG. 18B, a displacement of about 21 micrometers (µm) is increased to about 196 µm by the action of the amplification mechanism. Thus, with the amplification of the motion of the two moveable mirrors the total motion is about 392 µm, which provides an interferometric spectral resolution of about 12.7 cm$^{-1}$ over the mid-IR spectral range of 2000-500 cm$^{-1}$.

Figure 19A:
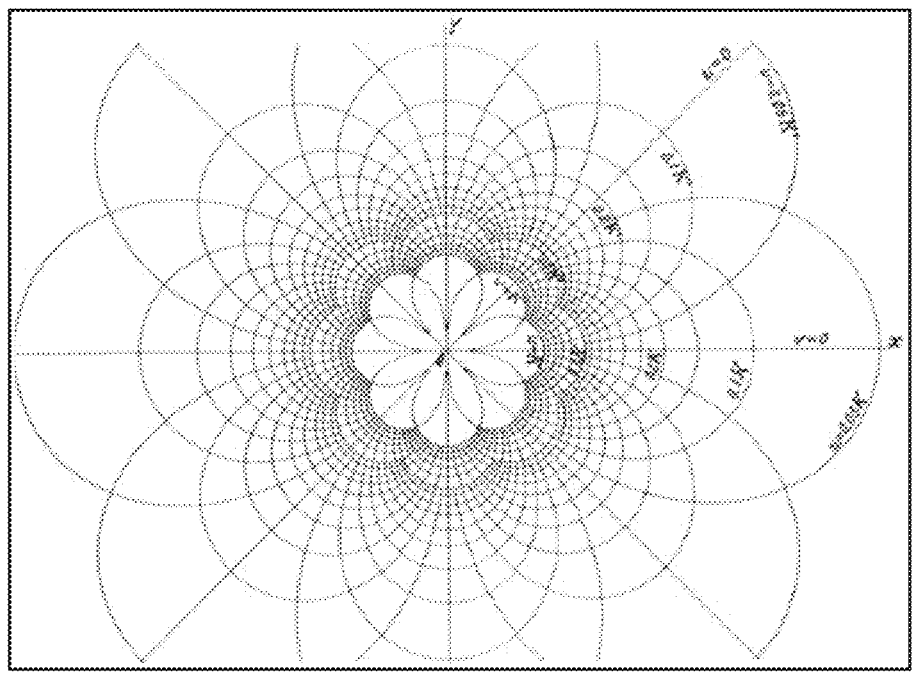
Figure 19B:
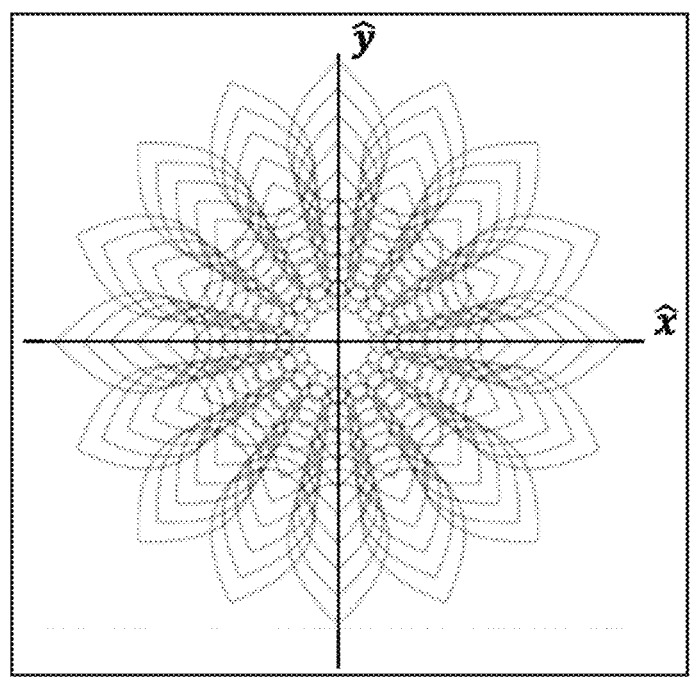

FIGS. 19A, 19B, 19C, and 19D are drawings showing a metasurface geometry of the microbolometer or detector 130 based on a geometric inversion of the Rhodonea conformal mapping contours. In this embodiment, the metasurface is derived from a geometric inversion of the Rhodonea conformal mapping contours, shown in FIG. 19A. FIG. 19B shows the pattern after geometrical inversion of the base conformal contours. The metasurface detector is based upon an electrically conductive geometric pattern imprinted onto the surface of a dielectric substrate ($Si_3N_4$) then both formed on a single layer of thermometric material ($VO_2$) using the pattern of FIG. 19B. FIG. 19C is a drawing of the final metasurface geometry formed along the inverted contours, wherein the dimensions are in microns. FIG. 19D is a magnified view of a portion of the metasurface, showing the patterns used for the present wavenumber range. The metasurface develops more than 90% infrared absorption in the biological fingerprint region, for example, in the wavenumber range of about 1500-600 cm$^{-1}$.

Figure 20A:
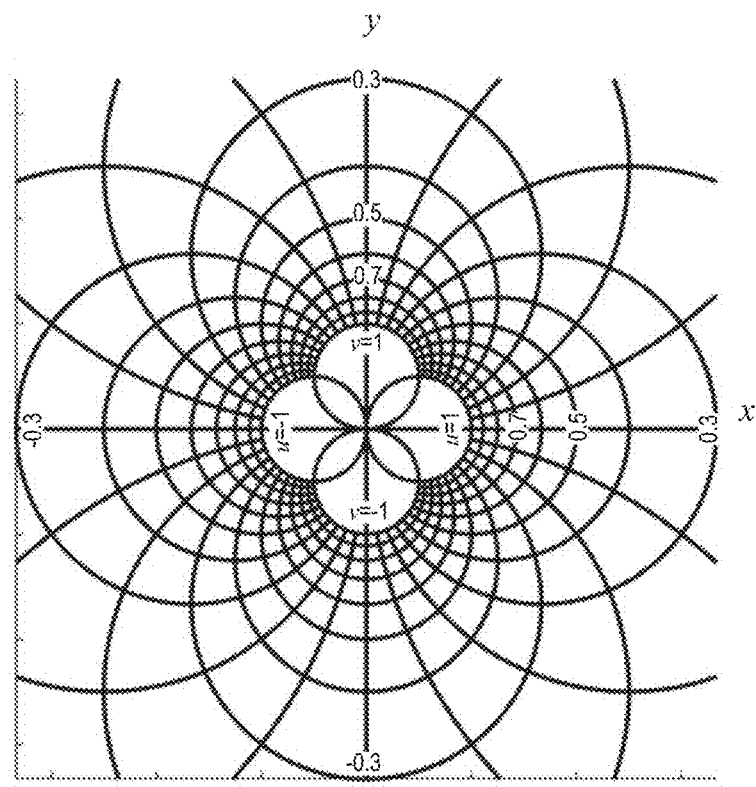
FIGS. 20A to 20D are drawings showing a metasurface geometry of the microbolometer or detector based on Tangent Circles conformal mapping contours.
Figure 20B:
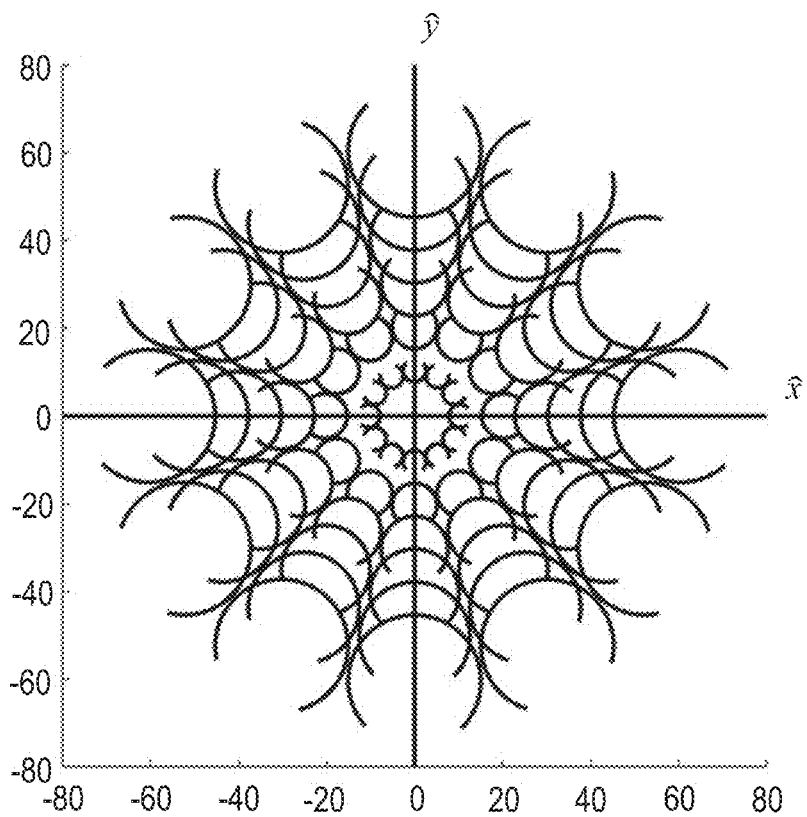
Figure 20D:
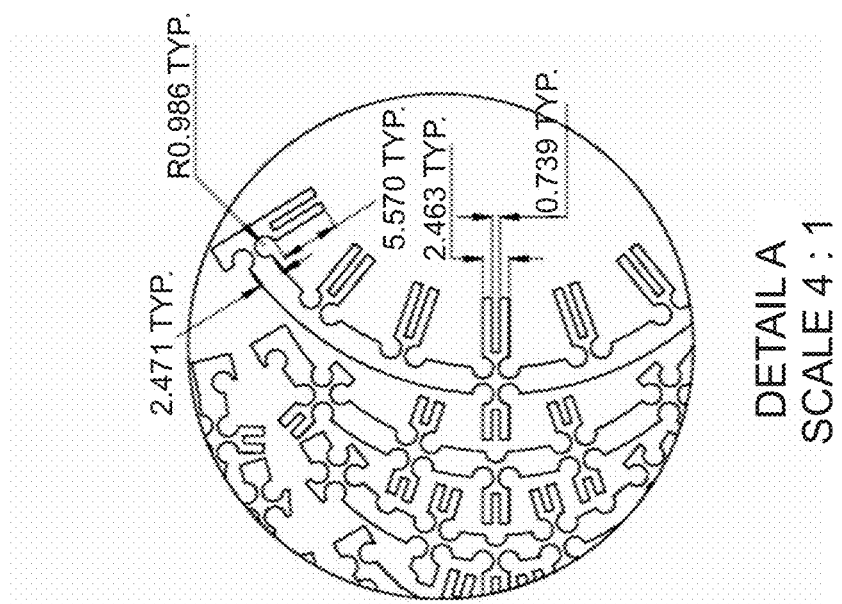
Figure 20C:
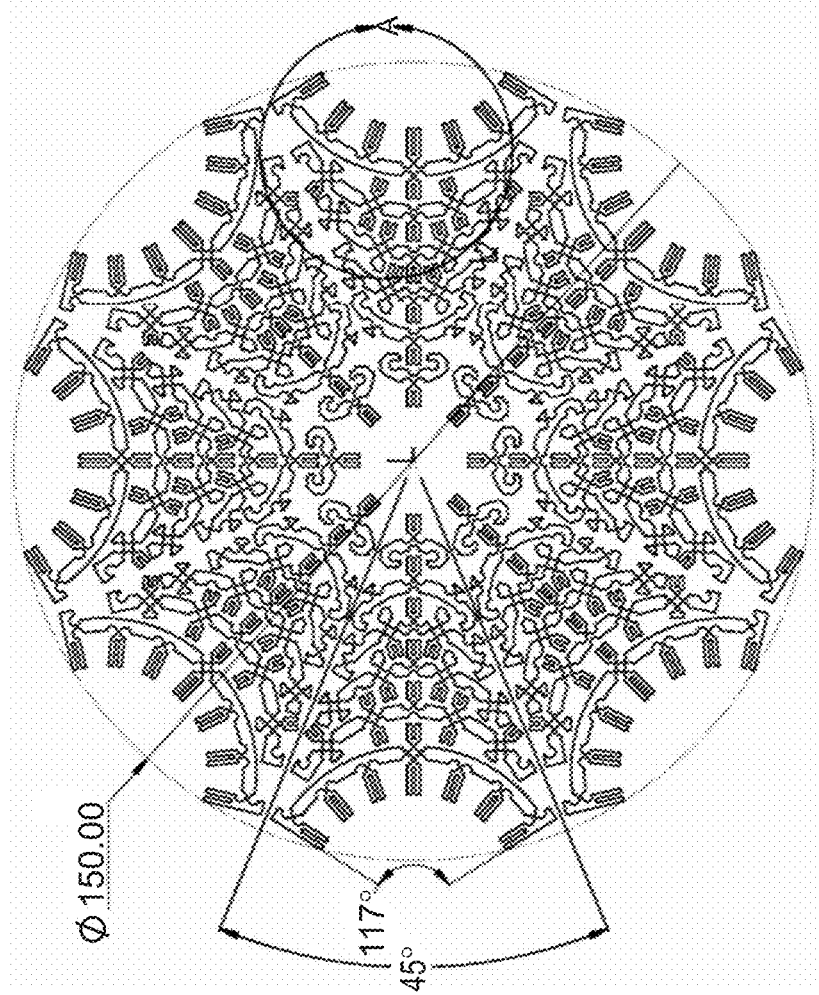

FIGS. 20A, 20B, 20C, and 20D are drawings showing a metasurface geometry of the microbolometer or detector 130 based on a geometric inversion of the Tangent Circles conformal mapping contours. In this embodiment, the metasurface is derived from a geometric inversion of a series of Tangent Circles conformal mapping contours, shown in FIG. 20A. FIG. 20B shows the pattern after geometrical inversion of the base conformal contours. The metasurface detector is based upon an electrically conductive geometric pattern imprinted onto the surface of a dielectric substrate ($Si_3N_4$) then both formed on a single layer of thermometric material ($VO_2$) using the pattern of FIG. 20B. FIG. 20C is a drawing of the final metasurface geometry formed along the inverted contours, wherein the dimensions are in microns. FIG. 20D is a magnified view of a portion of the metasurface, showing the patterns used for the present wavenumber range. The metasurface develops more than 90% infrared absorption in the biological fingerprint region, for example, in the wavenumber range of about 1500-600 cm$^{-1}$.

For both embodiments, the metasurface was found to exhibit a near zero index metamaterial behavior. The near zero index properties of the metasurface lead to an absorption phenomenon created by surface plasmon resonances. This phenomenon confines the absorption to the ultrathin metasurface, which makes the absorption properties of the detector practically independent of the material properties of the remaining materials that may comprise the microbolometer. This allows integration of the metasurface absorber with a common thermometric material layer, such as undoped vanadium dioxide ($VO_2$), which exhibits a metal-insulator-transition (MIT) region. In the region where the thermometric material is transitioning from an insulator to an electrically conductive metal, the thermometric properties improve by more than an order of magnitude. This allows for the performance of an uncooled detector technology to reach levels previously requiring active cooling.

The detector is based on the integration of the metasurface absorber in a microbolometer construction with a single $VO_2$ material thermometric layer that is temperature controlled to operate at 60° C., for example, within the metal-insulator-transition region. Within this transition region, the $VO_2$ layer has effectively transitioned from a dielectric to a metallic electrical conductor and acquires more than a 50-fold enhancement in the thermometric properties compared to the room temperature dielectric state. Thus, by controlling the detector cavity temperature at 60° C., the detectivity performance matches or exceeds conventional detector technologies cooled at cryogenic conditions, for example, at less than about −200° C. As a result, in some embodiments the detector technology described herein enables a downhole spectroscopic instrument with performance matching lab instruments. The uncooled microbolometer design exhibits a predicted maximum absorption of 99.5% at 870 cm$^{-1}$ and an absorption bandwidth of 150% FWHM on 1070 cm$^{-1}$ center wavenumber, coincident with important chemical spectra of downhole hydrocarbons.

Figure 21:
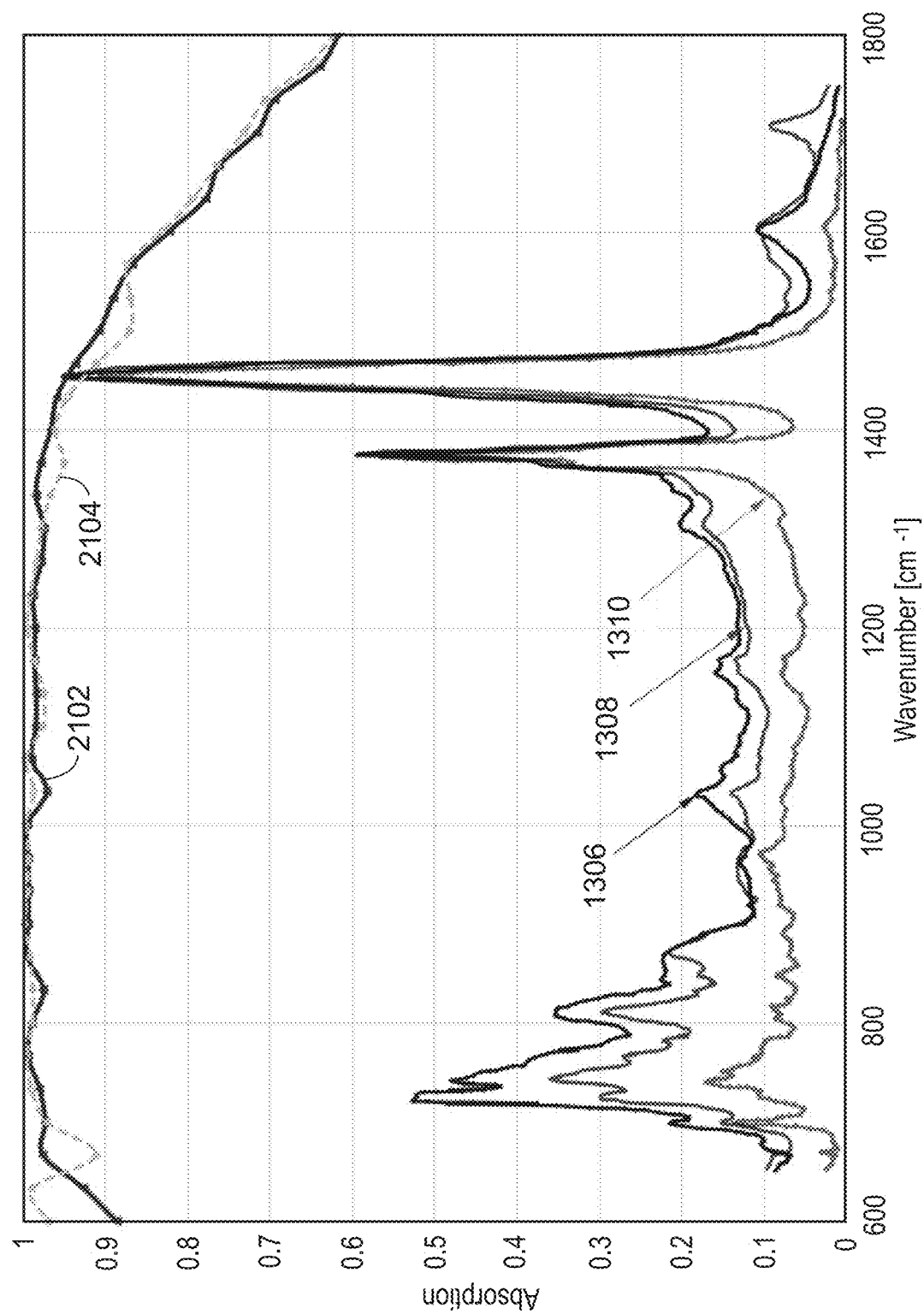
FIG. 21 is a plot showing the absorption spectrum for the three crude oils described with respect to FIGS. 13A-13B, compared to the absorption spectra for the two metasurface geometries.

FIG. 21 is a plot showing the absorption spectrum for the three crude oils 1306, 1308, and 1310, described with respect to FIGS. 13A and 13B, compared to the absorption spectra for the two metasurfaces. The absorption spectra for the metasurface 2102 based on the Rhodonea conformal mapping contours and the absorption spectrum 2104 for the metasurface based on the Tangent Circles conformal mapping contours are shown. The SARA fractions (saturate, aromatic, resin, and asphaltene) for the crude oil samples are summarized in Table 2. As can be seen in the plot, the detectivity 1302 of the metasurface detectors, using detectors with a 150 μm diameter formed from a layer of VO2 on Si3N4 would both be sufficiently high to characterize all three crude oil samples. The uncooled microbolometer as described with respect FIGS. 22A-22B, exhibits a predicted maximum absorption of 99.5% at 870 cm-1 and an absorption bandwidth of 150% full-width at half-maximum (FWHM) on 1070 cm-1 center wavenumber, coincident with important chemical spectra of downhole hydrocarbons as shown in the spectra overlay plot of FIG. 21. The spectra in FIG. 21 show the differences between crudes of different SARA fractions, and emphasize the high distinctions that exist in the lower wavenumber range below 1000 cm-1 in which the metasurface absorptivity remains generally above 95%.

Figure 22A:
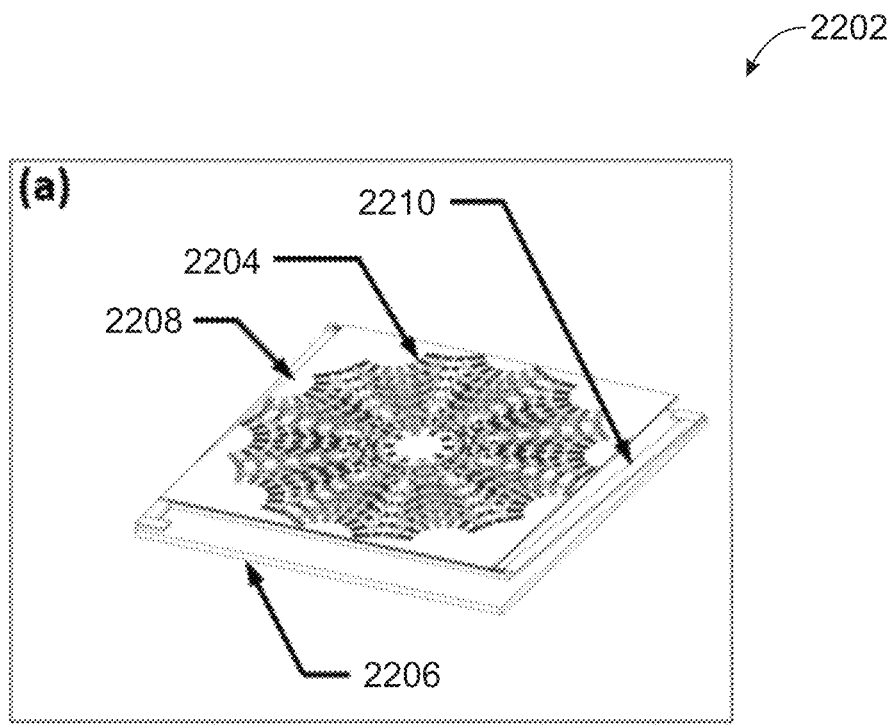
FIGS. 22A and 22B are drawings of an uncooled microbolometer using a metasurface geometry.
Figure 22B:
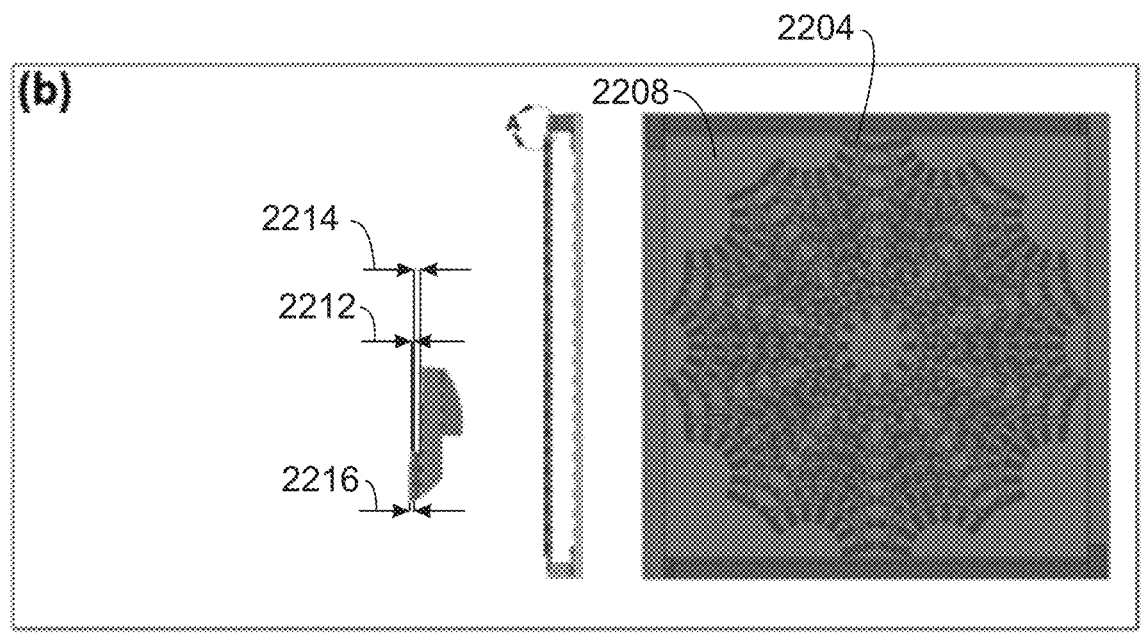

FIGS. 22A and 22B are drawings of an uncooled microbolometer 2202 using a metasurface geometry. In this embodiment, the metasurface is derived from a Rhodonea conformal mapping contours geometry as described with respect to FIGS. 19A to 19D. For in situ downhole chemical analysis applications, a sample rate on the order of once every second or so is minimally acceptable. For the 12.7 cm$^{-1}$ resolution achievable with the described MEMS FT-MIR interferometer and a minimum modulation frequency of 500 Hz, a 1 Hz sample rate to analyze the chemical spectral range of about 2000-500 cm$^{-1}$ constrains the system to using only four interferogram sweeps per sample. This limited number of interferogram sweeps may not provide sufficiently low noise levels in the analysis spectra and the eventual applications may constrain the operation to lower frequency sample rates below 1 Hz.

Thus, in some embodiments, a much higher modulation frequency is used. For a 1000 Hz modulation frequency, the corresponding number of interferogram sweeps increases to eight, which should provide a lower noise level in the analysis spectra. This option though does degrade the detectivity of the sensor by about 35% so a trade-off in analysis would be required.

The change in resistance of the thermometric layer due to a temperature change caused by the absorption of radiation by the metasurface 2204 is the response (or intensity) measured by the readout integrated circuit (ROIC) 2206 in the form of a change in voltage drop across the contacts of the bridge under constant bias current. The bridge structure, including the metasurface 2204, dielectric substrate 2208 and the thermometric layer (located underneath the dielectric substrate 2208), is suspended over the ROIC 2206 with an air gap using a set of thermal isolators 2210 in order to minimize the thermal conduction path to heat generated in the absorbing layer, allowing the ROIC 2206 to compound the effects of incident radiation and enhance the electrical signal created in response to changing field thermography.

A reduced thermal conduction path, though, must be balanced against increasing the thermal time constant and reducing the responsiveness to changing incident radiation. The mass of the bridge structure can be reduced in order to improve the response time, but may decrease electromagnetic absorptivity and increase voltage noise level on the detector. More rapid frame rates limit responsivity and detectivity while increased temperatures contribute to noise levels. Thus, high performance applications involving near-background radiation limited performance at rapid frame rates have been limited in practice to systems with active cooling. The predicted detector performance characteristics from integration of the inverted Rhodonea geometry metasurface into a conventional uncooled microbolometer architecture can be determined, providing a figure of merit. A similar figure of merit may be determined for a metasurface detector based on a Tangent Circles curve.

Detector Figures of Merit

In order to make a normalized comparison of the performance of different detectors, three parameters are generally used as figures of merit. These are voltage responsivity ($R_v$), signal to noise detectivity ($D^*$), and total voltage noise level, usually given in terms of a noise equivalent difference temperature (NEDT). The voltage responsivity, $R_v$, is a function of the output voltage signal and the temperature responsivity with changes in incident electromagnetic flux on the detector, and is given by the relation shown in Equation 1.

$$R_v = I_b R \beta R_T = I_b R \beta \frac{\Delta T}{\Delta \psi_0} \tag{1}$$

In Equation 1, $I_b$ is the bias current (amps, A), R is the bolometer electrical resistance (ohms, Ω), β is the thermometric layer temperature coefficient of resistance (TCR, 1/K), $R_T$ is the temperature responsivity of the detector (K/W), ΔT is the complex variation in temperature of the detector (K), and $\Delta \varphi_0$ is the complex variation in incident radiation (W).

The detector signal to noise detectivity $D^*$ is defined as shown in Equation 2.

$$D^* = R_x \sqrt{\frac{A_d}{4kTR + \alpha_H \left[\frac{I_b^2 R^2}{Nf}\right]}} \tag{2}$$

In equation 2, $A_d$ is the detector area confronting the incident radiation, k=1.38×10$^{-23}$ n-m/K (Boltzmann's constant), T is the absolute temperature (K) of the bridge structure, $\alpha_H$=0.002 (Hooge coefficient for homogenous semiconductor films), f is the modulation frequency, and N is the number of free carriers (electrons) in the thermometric material.

The noise equivalent difference temperature (NEDT) denotes the temperature change of a detector due to incident radiation that corresponds to an output signal equal to the RMS total noise level (a signal-to-noise ratio of 1). This is a fundamental parameter of the detector performance and represents the minimum temperature difference that can be discerned above the background noise. The NEDT is defined as shown in Equation 3.

$$NEDT = \Delta V_n \frac{\Delta T}{\Delta V_s} = \Delta V_n \frac{R_T}{R_v} \tag{3}$$

In Equation 3, $\Delta V_s$ is the voltage change for a temperature change of ΔT on the detector, and $\Delta V_n$ is the root mean square (RMS) total noise voltage level as calculated by the relation shown in Equation 4.

$$\frac{\Delta V_n^2}{\Delta f} = 4kTR + \alpha_H \left[\frac{I_b^2 R^2}{Nf}\right] \tag{4}$$

In equation 4, f is the modulation bandwidth.

In one embodiment, the metasurface detector design is based upon integration with a dielectric layer 1408 formed of a single layer of $Si_3N_4$ of about 200 nm in thickness 2212. The thermometric layer of $VO_2$, located under the dielectric substrate 2208, is about 500 nm in thickness 2214. This is enabled by the low mass loading of the metasurface 2204, which is a gold layer of about 120 nm in thickness 2216. Specifically, the metasurface geometry has a 35% fill factor within a 150 μm diameter. As used herein, fill factor represents the amount of active material in the pattern of the metasurface 2204, for example, the gold forming a metasurface.

In another embodiment, the detector 2202 has the dimensions shown in Table 3. In this embodiment, the thermometric layer of $VO_2$ is about 35 nm in thickness 2214, the dielectric substrate of $Si_3N_4$ is about 100 nm in thickness 2212, and the metasurface 2204 is about 27 nm in thickness 2216. As a result, the mass loading develops a maximum bending stress in the substrate of 6.3 kPa/g. The tensile strength of the $VO_2$ substrate is $\alpha_{ult}$=172 MPa giving an ultimate shock acceleration capability of greater than about 27000 g's, which is greater than required to sustain the expected worst case shock loads that could be experienced downhole in a production logging environment, for example, less than about 100 g's. As a result, confinement to single thermometric and dielectric layers is acceptable with this ultrathin metasurface for the expected downhole vibration and shock environments.

TABLE 3

Summary of metamaterial microbolometer design properties (f = 500 Hz, Δf = 10 Hz).

| | |
|---|---|
| $Si_3N_4$ dielectric substrate dimensions | 152 × 152 × 0.100 μm³ |
| $VO_2$ thermometric substate dimensions | 152 × 152 × 0.035 μm³ |
| Metasurface envelope | ø 150 × 0.027 μm³ |
| Maximum Absorption | 99.5% |
| Ti electrode dimensions (4) | 1 × 0.5 × 150 μm³ |
| Resistance, R | 9910 Ω |
| Bias Current, $I_b$ | 75 μA |
| Resistive Temperature Rise, $\Delta T_{I_b}$ | 2 K |
| TCR, β | 0.859 1/K @ 60° C. |
| Thermal Conductance, $G_{th}$ | 3.0 × 10⁻⁷ W/K |
| Thermal Capacitance, $C_{th}$ | 7.8 × 10⁻⁹ J/K |
| Thermal Time Constant, $\tau_{th}$ | 26 ms |
| NEDT | 1 mK |
| Maximum Responsivity, $R_v$ | 26 kV/W |
| Maximum Detectivity, D* | 1.06 × 10¹⁰ cm$\sqrt{Hz}$/W @ 500 Hz |

Figure 23A:
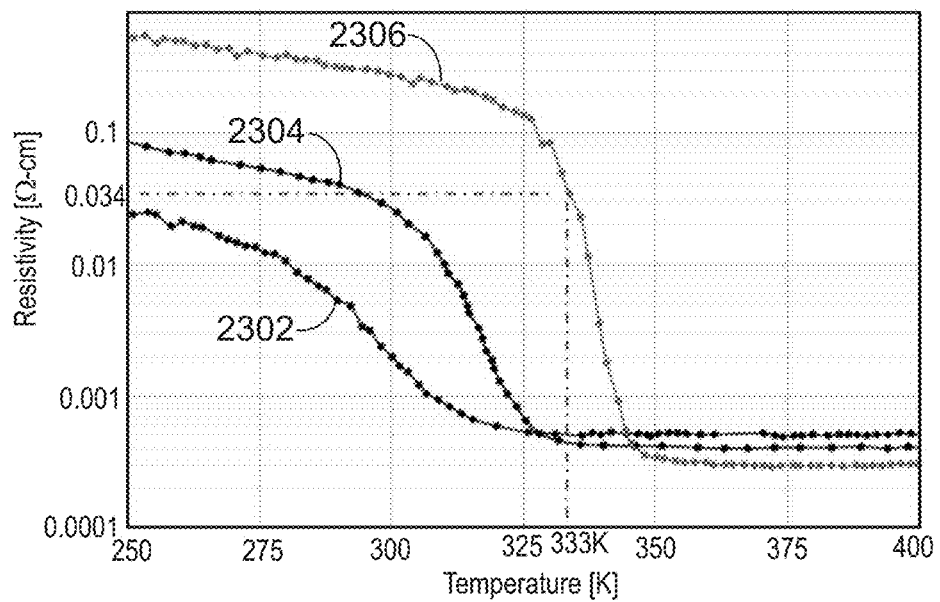
FIGS. 23A and 23B are plots showing a comparison of the thermal properties for doped vanadium oxide ($VO_2$) films and an undoped vanadium oxide ($VO_2$) film.
Figure 23B:
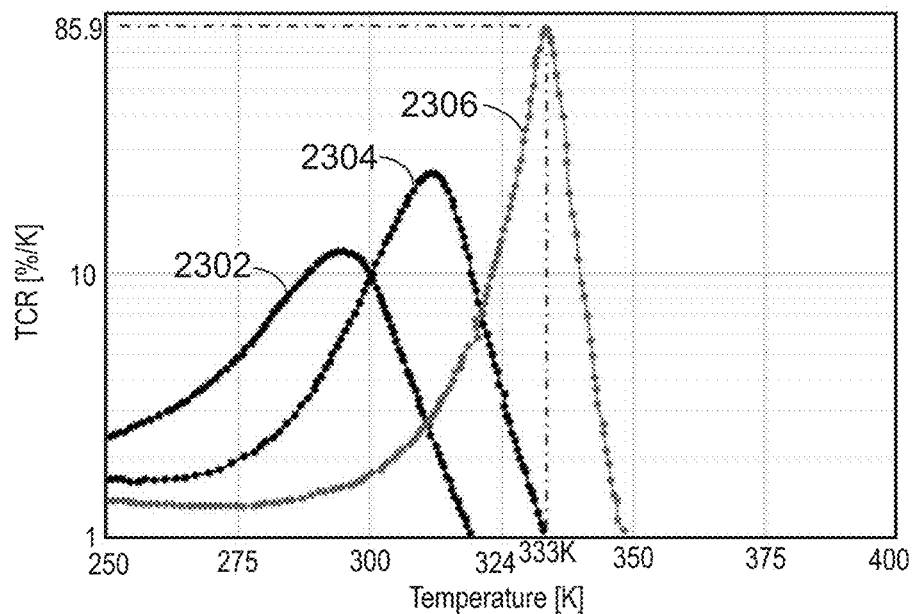

FIGS. 23A and 23B are plots showing a comparison of the thermal properties for doped vanadium oxide ($VO_2$) films 2302 and 2304 and an undoped vanadium oxide ($VO_2$) film 2306. FIG. 23A shows plots of the temperature dependence of electrical resistivity. FIG. 23B shows plots of the temperature dependence of the thermal coefficient of resistance (TCR).

The normalized detectivity (D*) as given by Equation 2 is dependent upon the electrical resistivity and thermal coefficient of resistance of the thermometric $VO_2$ layer, while the noise equivalent difference temperature (NEDT) as given by Equation 3 is dependent upon the specific carrier density. The plots in FIGS. 23A and 23B clearly illustrates the metal-insulation-transition (MIT). For undoped $VO_2$ film 2306, the data in FIG. 23A indicates a resistivity at 60° C. (333 K) of about 3.4×10⁻² Ω-cm. The theoretical electron density of $VO_2$ has been calculated to be about 4×10¹⁸/cm³. Using these material properties for the $VO_2$ thermometric layer, along with Equation 1 for responsivity $R_v$, Equation 2 for normalized detectivity (D*), and Equation 3 for noise equivalent difference temperature (NEDT) and simulation results for the metasurface absorptivity (using the MultiPhysics simulation software available from Comsol® of Stockholm, Sweden) predictions can be made for the metasurface detector performance figures of merit. Using the detector figures of merit as a set of discriminators, a series of analytical trade-off studies was conducted to optimize detector performance for a controlled detector cavity temperature of 60° C. and 500 Hz modulation frequency. The optimized detector figures of merit are detectivity (D*) of 1×10¹⁰ cm*sqrt (Hz)/W at 333 K, and an NEDT of 1 mK. The results are based upon 75 μA bias current, which creates a latent resistive temperature rise of 2.0 K in the microbolometer.

Figure 24:
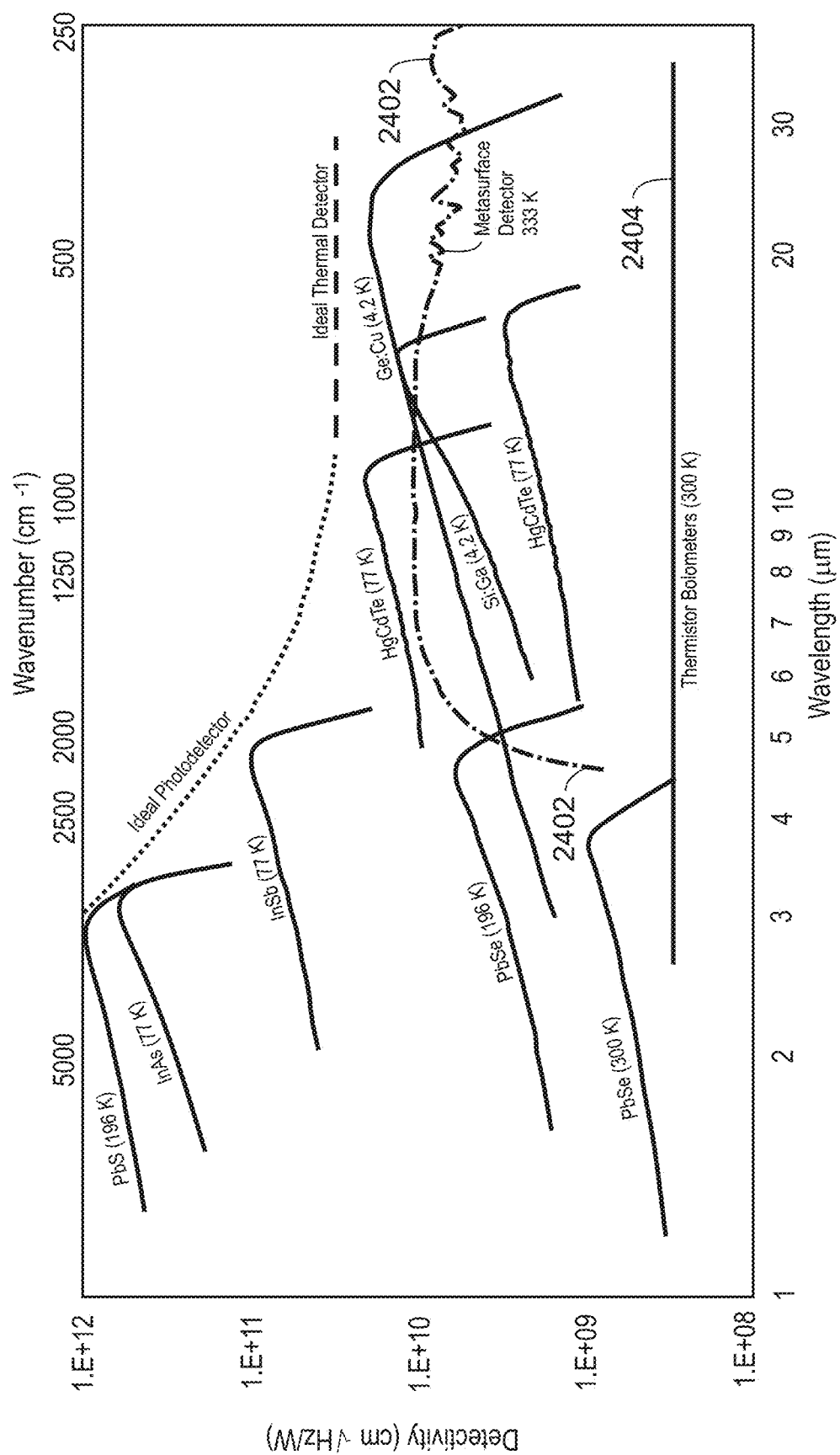
FIG. 24 is a plot showing a comparison of spectral response for the metasurface detector, based on Rhodonea conformal mapping contours, to various commercially available IR detectors operated at different temperatures.

FIG. 24 is a plot showing a comparison of spectral response for the metasurface detector 2402, based on the Rhodonea curve, to various commercially available IR detectors operated at different temperatures. The modulation frequency for all detectors is 1000 Hz, except for the state of the art uncooled thermistor bolometers 1604 at 10 Hz and the metasurface detector 1602 at 500 Hz.

The direct comparison in FIG. 24 includes the detectivity spectrum of the metasurface detector at 500 Hz modulation frequency superimposed onto the spectra for various commercially available infrared and THz detector technologies operated at the noted temperatures and over the wavenumber range from 10000-250 cm⁻¹. The superimposed metasurface microbolometer spectrum indicates a maximum detectivity D* of 1.0×10¹⁰ cm*sqrt (Hz)/W, which is comparable to the performance for the state of the art cryogenically cooled detectors.

Embodiments described herein provide a mid-IR perfect metasurface absorber (PMA) design, for example, formed from a geometric inversion of Rhodonea conformal mapping contours or Tangent Circles contours. The PMA behaves as a near zero index metamaterial having intrinsic multiple coupled absorption resonances that combine to form broadband infrared absorption characteristics of more than 90% in the wavenumber range 1500-600 cm⁻¹. An uncooled microbolometer design is described that uses the metasurface geometry imprinted on a single $Si_3N_4$ dielectric substrate with a single $VO_2$ thermometric substrate leading to a mid-IR detector with predicted maximum absorption of 99.5% at 870 cm⁻¹ and an absorption bandwidth of 156% full-width half-maximum (FWHM) on 1070 cm⁻¹ center wavenumber, coincident with important chemical spectra of downhole hydrocarbon fluids and emulsions. Figures of merit analyses for the uncooled microbolometer result in predicted maximum detectivity D*=1×10¹⁰ cm*sqrt (Hz)/W and noise equivalent difference temperature NEDT of 1 mK at a modulation frequency of 500 Hz and a microbolometer temperature of 60° C. These uncooled microbolometer parameters indicate mid-IR interferometers can be miniaturized for downhole applications of in situ FT-MIR spectroscopy.

Embodiments

An embodiment described in examples herein provides a miniature Fourier transform mid-infrared (FT-MIR) spectrometer. The FT-MIR includes a metasurface IR source to emit radiation when heated, a microelectromechanical (MEMS) interferometer, and a metasurface microbolometer to measure an interferogram from the MEMS interferometer, wherein the miniature FT-MIR spectrometer is less than about 20 mm in outer diameter.

In an aspect, the FT-MIR includes an attenuated total reflectance prism. In an aspect, the metasurface IR source includes an electrically conductive geometric pattern based on a geometric inversion of the Rhodonea conformal mapping contours. In an aspect, the metasurface IR source includes an electrically conductive geometric pattern based on a geometric inversion of the Tangent Circles conformal mapping contours.

In an aspect, the metasurface IR source is tuned to emit radiation from about 500 wavenumbers ($cm^{-1}$) to about 2000 $cm^{-1}$. In an aspect, wherein the metasurface IR source includes a heating filament to heat the metasurface IR source to about 900 K.

In an aspect, the MEMS interferometer, includes a pair of movable mirrors that are positioned along perpendicular axes, wherein each of the pair of movable mirrors is coupled to a mechanism including an electrostatic actuator driving a displacement amplification mechanism, and the displacement amplification mechanism driving each of the pair of the movable mirrors. The MEMS interferometer also includes a beam splitter positioned at an intersection of the perpendicular axes extending through each movable mirror and the beam splitter, and the metasurface microbolometer placed in line with the beam splitter to measure an intensity of a recombined beam from the pair of movable mirrors. In an aspect, the MEMS interferometer includes a single chip. In an aspect, the single chip is about 9.2 mm×9.2 mm.

In an aspect, the electrostatic actuator includes a central actuator attached to a movable comb, wherein the movable comb includes grounded tines, a positive comb including positive tines, wherein the positive tines are interspersed with the grounded tines on a first side of the movable comb. The electrostatic actuator also includes a negative comb including negative tines, wherein the negative tines are interspersed with the grounded tines on a second side of the movable comb. A sway stabilizer is attached to the central actuator at one end, and a coupling from the central actuator to the displacement amplification mechanism at an opposite end from the sway stabilizer.

In an aspect, the displacement amplification mechanism includes a symmetric fulcrum coupled to a central actuator of the electrostatic actuator, and three serpentine release flexures, wherein the serpentine release flexures allow moment release on the fulcrum to amplify the displacement from the central actuator to increase a motion of the movable mirror. In an aspect, the displacement amplification mechanism increases the motion of the movable mirror by a factor of nine over the motion of the central actuator.

In an aspect, the metasurface microbolometer includes a metasurface tuned to adsorb radiation in a range of frequencies in the mid infrared and a thermometric layer in contact with the metasurface, wherein the thermometric layer changes in resistivity with temperature changes. The metasurface microbolometer includes a dielectric substrate supporting the thermometric layer and the metasurface, and a readout integrated circuit to measure a response from the thermometric layer including a voltage drop across the contacts of the bridge with a constant bias current.

In an aspect, the metasurface is tuned to adsorb radiation from about 500 wavenumbers ($cm^{-1}$) to about 2000 $cm^{-1}$. In an aspect, the metasurface includes gold. In an aspect, the metasurface absorbs light through surface plasmon resonances. In an aspect, the metasurface is about 120 nm in thickness. In an aspect, the metasurface is less than 30 nm in thickness. In an aspect, the metasurface has a diameter of about 150 µm. In an aspect, the metasurface has a 35% fill factor. In an aspect, the metasurface has a detectivity (D*) of about $1 \times 10^{10}$ cm*sqrt (Hz)/W at 333 K at a bias current of 75 µA. In an aspect, the metasurface has a noise equivalent difference temperature (NEDT) of about 1 mK at a bias current of 75 µA.

In an aspect, the thermometric layer includes undoped vanadium oxide ($VO_2$). In an aspect, the thermometric layer is about 500 nm in thickness. In an aspect, the dielectric substrate includes silicon nitride ($Si_3N_4$). In an aspect, the dielectric substrate is about 200 nm in thickness. In an aspect, the dielectric substrate is about 100 nm in thickness. In an aspect, the dielectric substrate is separated from the readout integrated circuit by an airgap.

In an aspect, the metasurface microbolometer has a broadband absorption of more than 90% in a wavenumber range of about 1500 to about 600 $cm^{-1}$. In an aspect, the metasurface microbolometer has an absorption bandwidth of 156% of full width half maximum (FWHM) centered on a wavenumber of 1070 $cm^{-1}$.

Other implementations are also within the scope of the following claims.

What is claimed is:

1. A miniature Fourier transform mid-infrared (FT-MIR) spectrometer, comprising:
    a metasurface IR source to emit radiation when heated;
    a microelectromechanical (MEMS) interferometer; and
    a metasurface microbolometer to measure an interferogram from the MEMS interferometer, wherein the miniature FT-MIR spectrometer is less than about 20 mm in outer diameter.

2. The miniature FT-MIR spectrometer of claim 1, comprising an attenuated total reflectance prism.

3. The miniature FT-MIR spectrometer of claim 1, wherein the metasurface IR source comprises an electrically conductive geometric pattern based on a geometric inversion of the Rhodonea conformal mapping contours.

4. The miniature FT-MIR spectrometer of claim 1, wherein the metasurface IR source comprises an electrically conductive geometric pattern based on a geometric inversion of the Tangent Circles conformal mapping contours.

5. The miniature FT-MIR spectrometer of claim 1, wherein the metasurface IR source is tuned to emit radiation from about 500 wavenumbers ($cm^{-1}$) to about 2000 $cm^{-1}$.

6. The miniature FT-MIR spectrometer of claim 1, wherein the metasurface IR source comprises a heating filament to heat the metasurface IR source to about 900 K.

7. The miniature FT-MIR spectrometer of claim 1, wherein the MEMS interferometer, comprises:
    a pair of movable mirrors that are positioned along perpendicular axes, wherein each of the pair of movable mirrors is coupled to a mechanism comprising:
      an electrostatic actuator driving a displacement amplification mechanism; and
      the displacement amplification mechanism driving each of the pair of the movable mirrors; and
    a beam splitter positioned at an intersection of the perpendicular axes extending through each movable mirror and the beam splitter; and
    the metasurface microbolometer placed in line with the beam splitter to measure an intensity of a recombined beam from the pair of movable mirrors.

8. The miniature FT-MIR spectrometer of claim 7, wherein the MEMS interferometer comprises a single chip.

9. The miniature FT-MIR spectrometer of claim 8, wherein the single chip is about 9.2 mm×9.2 mm.

10. The miniature FT-MIR spectrometer of claim 7, wherein the electrostatic actuator comprises:
- a central actuator attached to a movable comb, wherein the movable comb comprise grounded tines;
- a positive comb comprising positive tines, wherein the positive tines are interspersed with the grounded tines on a first side of the movable comb;
- a negative comb comprising negative tines, wherein the negative tines are interspersed with the grounded tines on a second side of the movable comb;
- a sway stabilizer attached to the central actuator at one end; and
- a coupling from the central actuator to the displacement amplification mechanism at an opposite end from the sway stabilizer.

11. The miniature FT-MIR spectrometer of claim 7, wherein the displacement amplification mechanism comprises:
- a symmetric fulcrum coupled to a central actuator of the electrostatic actuator; and
- three serpentine release flexures, wherein the serpentine release flexures allow moment release on the fulcrum to amplify the displacement from the central actuator to increase a motion of the movable mirror.

12. The miniature FT-MIR spectrometer of claim 11, wherein the displacement amplification mechanism increases the motion of the movable mirror by a factor of nine over the motion of the central actuator.

13. The miniature FT-MIR spectrometer of claim 1, wherein the metasurface microbolometer comprises:
- a metasurface tuned to adsorb radiation in a range of frequencies in the mid infrared;
- a thermometric layer in contact with the metasurface, wherein the thermometric layer changes in resistivity with temperature changes;
- a dielectric substrate supporting the thermometric layer and the metasurface; and
- a readout integrated circuit to measure a response from the thermometric layer comprising a voltage drop across the contacts of the bridge with a constant bias current.

14. The miniature FT-MIR spectrometer of claim 13, wherein the metasurface is tuned to adsorb radiation from about 500 wavenumbers ($cm^{-1}$) to about 2000 $cm^{-1}$.

15. The miniature FT-MIR spectrometer of claim 13, wherein the metasurface comprises gold.

16. The miniature FT-MIR spectrometer of claim 13, wherein the metasurface absorbs light through surface plasmon resonances.

17. The miniature FT-MIR spectrometer of claim 13, wherein the metasurface is about 120 nm in thickness.

18. The miniature FT-MIR spectrometer of claim 13, wherein the metasurface is less than 30 nm in thickness.

19. The miniature FT-MIR spectrometer of claim 13, wherein the metasurface has a diameter of about 150 μm.

20. The miniature FT-MIR spectrometer of claim 13, wherein the metasurface has a 35% fill factor.

21. The miniature FT-MIR spectrometer of claim 13, wherein the metasurface has a detectivity (D*) of about $1 \times 10^{10}$ cm*sqrt (Hz)/W at 333 K at a bias current of 75 μA.

22. The miniature FT-MIR spectrometer claim 13, wherein the metasurface has a noise equivalent difference temperature (NEDT) of about 1 mK at a bias current of 75 μA.

23. The miniature FT-MIR spectrometer of claim 13, wherein the thermometric layer comprises undoped vanadium oxide ($VO_2$).

24. The miniature FT-MIR spectrometer of claim 13, wherein the thermometric layer is about 500 nm in thickness.

25. The miniature FT-MIR spectrometer of claim 13, wherein the dielectric substrate comprises silicon nitride ($Si_3N_4$).

26. The miniature FT-MIR spectrometer of claim 13, wherein the dielectric substrate is about 200 nm in thickness.

27. The miniature FT-MIR spectrometer of claim 13, wherein the dielectric substrate is about 100 nm in thickness.

28. The miniature FT-MIR spectrometer of claim 13, wherein the dielectric substrate is separated from the readout integrated circuit by an airgap.

29. The miniature FT-MIR spectrometer of claim 13, wherein the metasurface microbolometer has a broadband absorption of more than 90% in a wavenumber range of about 1500 to about 600 $cm^{-1}$.

30. The miniature FT-MIR spectrometer of claim 1, wherein the metasurface microbolometer has an absorption bandwidth of 156% of full width half maximum (FWHM) centered on a wavenumber of 1070 $cm^{-1}$.

* * * * *